United States Patent [19]

Schollkopf et al.

[11] Patent Number: 5,973,172
[45] Date of Patent: Oct. 26, 1999

[54] 14-α,17-α-C$_2$-BRIDGED NORPROGESTERONE DERIVATIVES

[75] Inventors: Klaus Schollkopf; Wolfgang Halfbrodt; Joachim Kuhnke; Wolfgang Schwede; Karl-Heinrich Fritzemeier; Rolf Krattenmacher; Hans-Peter Muhn, all of Berlin, Germany

[73] Assignee: Schering Akitengesellschaft, Berlin, Germany

[21] Appl. No.: 09/135,483

[22] Filed: Aug. 18, 1998

Related U.S. Application Data

[62] Division of application No. 08/578,847, Dec. 26, 1995, Pat. No. 5,827,842.

[30] Foreign Application Priority Data

Dec. 23, 1994 [DE] Germany ............... 44 47 401

[51] Int. Cl.$^6$ .............. C07J 53/00; C07J 71/00
[52] U.S. Cl. .............. 552/510; 540/15; 540/16; 540/60; 540/62
[58] Field of Search .............. 540/15, 16, 60, 540/62; 552/510

[56] References Cited

PUBLICATIONS

A.J. Solo et al., Steroids: Structure, Function and Regulation, 18:251–259 (Sept. 1971).
A.J. Solo et al., Journal of Medicinal Chemistry, 16:270–273 (Mar. 1973).
J.R. Bull et al., South African Journal of Chemistry, 44:87–94 (Sept. 1991).
A.J. Solo et al., Journal of Pharmaceutical Sciences, 62:1471–1475 (Sept. 1973).

*Primary Examiner*—Jose' G. Dees
*Assistant Examiner*—Barbara Badio
*Attorney, Agent, or Firm*—Millen, White, Zelano & Branigan, P.C.

[57] ABSTRACT

The invention describes 14,17-C$_2$-bridged steroids of general formula (I),

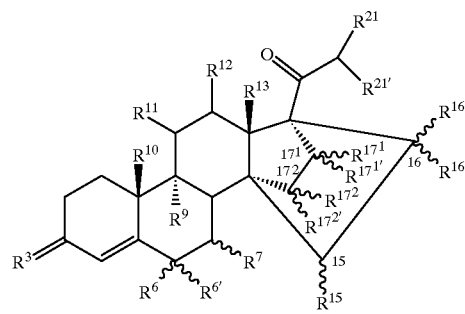

wherein the various R groups are as defined in the specification, and wherein said steroids are in contrast, with the disclaimed compound, the new compounds are available even after peroral administration with high gestagenic action and are suitable for the production of pharmaceutical agents.

9 Claims, No Drawings

14-α,17-α-C₂-BRIDGED NORPROGESTERONE DERIVATIVES

This is a division, of application Ser. No. 08/578,847 filed Dec. 26, 1995, now U.S. Pat. No. 5,827,842.

This invention relates to 14,17-$C_2$-bridged steroids of general formula (I),

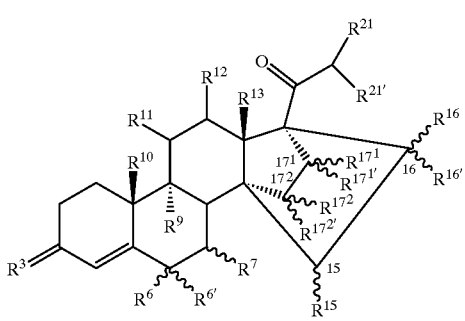

in which $R^3$ stands for an oxygen atom, the hydroxyimino group or two hydrogen atoms, $R^6$ stands for a hydrogen, fluorine, chlorine or bromine atom or for a $C_1$–$C_4$ alkyl radical in α- or β-position, and then $R^{6'}$ and $R^7$ represent hydrogen atoms, or else $R^6$ stands for a hydrogen, fluorine, chlorine or bromine atom, or for a $C_1$–$C_4$ alkyl radical, and then $R^{6'}$ and $R^7$ represent a common additional bond, $R^7$ stands for a $C_1$–$C_4$ alkyl radical in α- or β-position, and then $R^6$ and $R^{6'}$ represent hydrogen atoms, or else $R^6$ and $R^7$ together stand for a methylene group in α- or β-position and $R^{6'}$ stands for a hydrogen atom or $R^6$ and $R^{6'}$ together stand for an ethylene or methylene group and $R^7$ stands for a hydrogen atom, $R^9$ and $R^{10}$ each stand for a hydrogen atom or a common bond, $R^{11}$ and $R^{12}$ each stand for a hydrogen atom or a common bond, $R^{13}$ stands for a methyl or ethyl group, $R^{15}$ stands for a hydrogen atom or a $C_1$–$C_3$ alkyl radical, $R^{16}$ and $R^{16'}$, independently of one another, stand for a hydrogen atom, a $C_1$–$C_3$ alkyl radical or a $C_2$–$C_4$ alkenyl radical or together for a $C_1$–$C_3$ alkylidene group, $R^{15}$ and $R^{16}$ stand for a common bond and $R^{16'}$ stands for a hydrogen atom or a $C_1$–$C_3$ alkyl radical or $R^{15}$ and $R^{16}$ together stand for a ring of partial formula

in which n=1 and 2 and X means a methylene group or an oxygen atom, and $R^{16'}$ stands for a hydrogen atom, $R^{17^1}$ stands for a hydrogen atom or a $C_1$–$C_3$ alkyl radical, $R^{17^2}$ stands for a hydrogen atom, a $C_1$–$C_3$ alkyl radical or a $C_2$–$C_4$ alkenyl radical, $R^{17^{1'}}$ and $R^{17^{2'}}$ each stand for a hydrogen atom or for a common bond, $R^{21}$ stands for a hydrogen atom or a $C_1$–$C_3$ alkyl radical, $R^{21'}$ stands for a hydrogen atom, a $C_1$–$C_3$ alkyl radical or a hydroxy group, except for the compound 14,17-ethano-19-norpregn-4-ene-3,20-dione.

The wavy lines

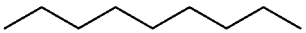

in the general formulas of this invention mean that the substituent in question can be present in α- or β-position on the corresponding carbon atom.

In the case of the $C_1$–$C_3$ alkyl groups, referred to above as possible substituents, it can be a methyl, ethyl, n-propyl or i-propyl group, and in the case of the $C_1$–$C_4$ alkyl groups, in addition this can be an n-butyl, i-butyl or tert-butyl group. In all cases, a methyl or ethyl group is preferred.

In the case of the $C_2$–$C_4$ alkenyl radical for $R^{16}$, $R^{16'}$ and/or $R^{17^2}$, this is a vinyl, allyl or but-3-enyl radical; the vinyl radical is preferred.

Preferred according to this invention are those compounds of general formula (I), in which $R^3$ stands for an oxygen atom or two hydrogen atoms, and/or $R^6$ stands for a hydrogen atom or $R^6$ stands for a $C_1$–$C_4$ alkyl radical in α- or β-position, if $R^{6'}$ and $R^7$ represent hydrogen atoms, or else $R^6$ stands for a hydrogen, chlorine or bromine atom or $R^6$ stands for a $C_1$–$C_4$ alkyl radical, if $R^{6'}$ and $R^7$ represent a common additional bond and/or $R^{16}$ and $R^{16'}$ each stand for a hydrogen atom, each stand for a methyl group or one of these two substituents stands for a $C_1$–$C_4$ alkyl group or a vinyl group and the other of these two substituents stands for a hydrogen atom, or both together for a $C_1$–$C_3$ alkylidene group and/or $R^{17^1}$ and $R^{17^2}$, independently of one another, stand for a hydrogen atom or a methyl group and/or $R^{17^{1'}}$ and $R^{17^{2'}}$ each stand for a hydrogen atom or a common bond and/or $R^{21}$ stands for a hydrogen atom or a $C_1$–$C_3$ alkyl radical and $R^{21'}$ stands for a hydrogen atom or a hydroxy group and the other substituents all can have the meanings indicated in formula (I).

The compounds mentioned below are especially preferred according to the invention:

14,17-Ethano-19-norpregna-4,9-diene-3,20-dione;
14,17-ethano-19-norpregna-4,6-diene-3,20-dione;
14,17-ethano-19-norpregna-4,15-diene-3,20-dione;
14,17-ethano-19-norpregna-4,6,15-triene-3,20-dione;
14,17-ethano-19-norpregna-4,9,15-triene-3,20-dione;
21-methyl-14,17-ethano-19-norpregn-4-ene-3,20-dione;
21-methyl-14,17-ethano-19-norpregna-4,9-diene-3,20-dione;
21-methyl-14,17-ethano-19-norpregna-4,6-diene-3,20-dione;
21-methyl-14,17-ethano-19-norpregna-4,15-diene-3,20-dione;
21-methyl-14,17-ethano-19-norpregna-4,9,15-triene-3,20-dione;
14,17-etheno-19-norpregn-4-ene-3,20-dione;
14,17-etheno-19-norpregna-4,6-diene-3,20-dione;
14,17-etheno-19-norpregna-4,9-diene-3,20-dione;
21-methyl-14,17-etheno-19-norpregn-4-ene-3,20-dione;
21-methyl-14,17-etheno-19-norpregna-4,6-diene-3,20-dione;
21-methyl-14,17-etheno-19-norpregna-4,9-diene-3,20-dione;

21-methyl-14,17-etheno-19-norpregna-4,9,11-triene-3,20-dione;
21-hydroxy-14,17-etheno-19-norpregn-4-ene-3,20-dione;
21-hydroxy-14,17-etheno-19-norpregna-4,9-diene-3,20-dione;
17$^1$-methyl-14,17-etheno-19-norpregn-4-ene-3,20-dione;
17$^1$-methyl-14,17-etheno-19-norpregna-4,6-diene-3,20-dione;
17$^2$-methyl-14,17-etheno-19-norpregn-4-ene-3,20-dione;
17$^2$-methyl-14,17-etheno-19-norpregna-4,9-diene-3,20-dione;
15β,16α-dimethyl-14,17-etheno-19-norpregn-4-ene-3,20-dione;
6-methyl-14,17-ethano-19-norpregna-4,6-diene-3,20-dione;
6-chloro-14,17-ethano-19-norpregna-4,6-diene-3,20-dione;
6α-methyl-14,17-ethano-19-norpregn-4-ene-3,20-dione;
6,21-dimethyl-14,17-ethano-19-norpregna-4,6-diene-3,20-dione;
15β,16α-dimethyl-14,17-ethano-19-norpregn-4-ene-3,20-dione;
6-chloro-21-methyl-14,17-ethano-19-norpregna-4,6-diene-3,20-dione;
16α-methyl-14,17-ethano-19-norpregn-4-ene-3,20-dione;
16α-methyl-14,17-ethano-19-norpregna-4,6-diene-3,20-dione;
16α-methyl-14,17-ethano-19-norpregna-4,9-diene-3,20-dione;
16α,21-dimethyl-14,17-ethano-19-norpregna-4,9-diene-3,20-dione;
21-hydroxy-16α-methyl-14,17-ethano-19-norpregn-4-ene-3,20-dione;
16α-ethyl-14,17-ethano-19-norpregn-4-ene-3,20-dione;
16α-ethenyl-14,17-ethano-19-norpregn-4-ene-3,20-dione;
16-methyl-14,17-ethano-19-norpregna-4,15-diene-3,20-dione;
(17$^1$R)-17$^1$-methyl-14,17-ethano-19-norpregn-4-ene-3,20-dione;
(17$^1$S)-17$^1$-methyl-14,17-ethano-19-norpregn-4-ene-3,20-dione;
(17$^1$R)-17$^1$-methyl-14,17-ethano-19-norpregna-4,9-diene-3,20-dione;
(17$^1$S)-17$^1$-methyl-14,17-ethano-19-norpregna-4,9-diene-3,20-dione
(17$^2$R)-17$^2$-methyl-14,17-ethano-19-norpregn-4-ene-3,20-dione;
(17$^2$R)-17$^2$-methyl-14,17-ethano-19-norpregna-4,6-diene-3,20-dione;
(17$^2$R)-17$^2$-methyl-14,17-ethano-19-norpregna-4,9-diene-3,20-dione;
(17$^2$R)-17$^2$,21-dimethyl-14,17-ethano-19-norpregna-4,6-diene-3,20-dione;
(17$^2$R)-17$^2$,21-dimethyl-14,17-ethano-19-norpregna-4,9-diene-3,20-dione;
(17$^2$R)-17$^2$,21-dimethyl-14,17-ethano-19-norpregna-4,9,11-triene-3,20-dione;
16-methylene-14,17-ethano-19-norpregn-4-ene-3,20-dione;
16-methylene-14,17-ethano-19-norpregna-4,6-diene-3,20-dione;
16-methylene-14,17-ethano-19-norpregna-4,9-diene-3,20-dione;
21-hydroxy-14,17-ethano-19-norpregn-4-ene-3,20-dione;
21-hydroxy-14,17-ethano-19-norpregna-4,6-diene-3,20-dione;
21-hydroxy-14,17-ethano-19-norpregna-4,9-diene-3,20-dione;
21-hydroxy-14,17-ethano-19-norpregna-4,9,15-triene-3,20-dione;
(21R)-21-hydroxy-21-methyl-14,17-ethano-19-norpregn-4-ene-3,20-dione;
(21S)-21-hydroxy-21-methyl-14,17-ethano-19-norpregn-4-ene-3,20-dione;
(21R)-21-hydroxy-21-methyl-14,17-ethano-19-norpregna-4,9-diene-3,20-dione;
(21S)-21-hydroxy-21-methyl-14,17-ethano-19-norpregna-4,9-diene-3,20-dione;
(21R)-21-hydroxy-21-methyl-14,17-ethano-19-norpregna-4,6-diene-3,20-dione;
(21S)-21-hydroxy-21-methyl-14,17-ethano-19-norpregna-4,6-diene-3,20-dione;
(21R)-21-hydroxy-21-methyl-14,17-ethano-19-norpregna-4,9,15-triene-3,20-dione;
(21S)-21-hydroxy-21-methyl-14,17-ethano-19-norpregna-4,9,15-triene-3,20-dione;
14,17-ethano-18a-homo-19-norpregn-4-ene-3,20-dione;
14,17-ethano-18a-homo-19-norpregna-4,6-diene-3,20-dione;
14,17-ethano-18a-homo-19-norpregna-4,9-diene-3,20-dione;
14,17-ethano-18a-homo-19-norpregna-4,15-diene-3,20-dione;
21-methyl-14,17-ethano-18a-homo-19-norpregn-4-ene-3,20-dione;
21-methyl-14,17-ethano-18a-homo-19-norpregna-4,6-diene-3,20-dione;
21-methyl-14,17-ethano-18a-homo-19-norpregna-4,9-diene-3,20-dione;
(21R)-21-hydroxy-21-methyl-14,17-ethano-18a-homo-19-norpregn-4-ene-3,20-dione;
(21S)-21-hydroxy-21-methyl-14,17-ethano-18a-homo-19-norpregn-4-ene-3,20-dione;
(21R)-21-hydroxy-21-methyl-14,17-ethano-18a-homo-19-norpregna-4,9-ene-3,20-dione;
(21S)-21-hydroxy-21-methyl-14,17-ethano-18a-homo-19-norpregna-4,9-ene-3,20-dione;
(21R)-21-hydroxy-21-methyl-14,17-ethano-18a-homo-19-norpregna-4,6-ene-3,20-dione;
(21S)-21-hydroxy-21-methyl-14,17-ethano-18a-homo-19-norpregna-4,6-ene-3,20-dione;

In the gestagen receptor bonding test on gestagenic action when using cytosol from rabbit uterus homogenate and $^3$H-progesterone as reference substance, the new compounds show a very strong affinity to the gestagen receptor. In the pregnancy maintenance test on the rat, the compounds of general formula (I) according to the invention show a very high gestagenic activity. The compounds of general formula (I) also show effects on other steroid receptors.

14,17-Ethano-19-norpregn-4-ene-3,20-dione, the compound which is disclaimed from the scope of general formula I, was described by A. J. Solo and J. N. Kapoor in J. Med. Chem. 16, 270 (1973). In the endometrium transformation test (Clauberg Test) on gestagenic action, this compound has a good effect after subcutaneous administration, but only a slight effect after oral administration. The factor between subcutaneous and peroral action is over 20 according to the above-mentioned bibliographic reference.

In addition to very high gestagenic action in the pregnancy maintenance test, which for the most part exceeds even that of the disclaimed compound, the compounds of general formula I according to the invention show a good gestagenic action in contrast to the already known compound 14,17-ethano-19-norpregn-4-ene-3,20-dione, but for the most part also after oral administration. The factor between subcutaneous and peroral action is approximately between 3 and 5 for the compounds according to the invention. The compounds according to the invention are thus distinguished from the disclaimed compound by a significantly improved spectrum of activity.

Based on their high gestagenic action, the new compounds of general formula (I), for example, alone or in combination with estrogens, can be used in preparations for contraception. Also all other possibilities of use now known for gestagens, however, are open to the new compounds.

The dosage of the compounds according to the invention in contraceptive preparations is preferably 0.01–2 mg per day. Suitable dosages can be routinely determined, e.g., by determining bioequivalence to a known gestagen for a particular use, e.g., an amount bioequivalent to 30–150 μg per day of levonorgestrel.

The gestagenic and estrogenic active ingredient components are preferably orally administered together in contraception preparations. The daily dose is preferably administered one time.

As estrogens, preferably synthetic estrogens such as ethinylestradiol, 14α,17α-ethano-1,3,5(10)-estratriene-3, 17β-diol (WO 88/01275) or 14α,17α-ethano-1,3,5(10)-estratriene-3,16α,17β-triol (WO 91/08219) are suitable.

The estrogen is administered in an amount that corresponds to that of 0.01 to 0.05 mg of ethinylestradiol.

The new compounds of general formula (I) can also be used in preparations for treating gynecological disorders and for substitution therapy. Because of their advantageous action profile, the compounds according to the invention are especially well suited for treating premenstrual symptoms, such as headaches, depressive moods, water retention and mastodynia. The daily dose in the case of treating premenstrual symptoms is approximately 1 to 20 mg.

Finally, the new compounds can also be used as gestagenic components in the compositions that have recently become known for female birth control, which are distinguished by the additional use of a competitive progesterone antagonist (H. B. Croxatto and A. M. Salvatierra in Female Contraception and Male Fertility Regulation, ed. by Runnebaum, Rabe & Kiesel—Vol. 2, Advances in Gynecological and Obstetric Research Series, Parthenon Publishing Group—1991, page 245).

The dosage is in the range already indicated, the formutation can be carried out as in conventional OC preparations. The administration of additional, competitive progesterone antagonists can also be made sequentially in this case.

The formulation of the pharmaceutical preparations based on new compounds is carried out in a way known in the art, by the active ingredient, optionally in combination with an estrogen, being processed with the vehicles, diluents, optionally flavoring additives, etc., that are commonly being used in galenicals and converted to the desired form of administration.

For the preferred oral administration, especially tablets, coated tablets, capsules, pills, suspensions or solutions are suitable.

For parenteral administration, especially oily solutions, such as, for example, solutions in sesame oil, castor oil and cottonseed oil, are suitable. To increase solubility, solubilizers, such as, for example, benzyl benzoate or benzyl alcohol, can be added.

The compounds of general formula (I) can also be administered continuously by an intrauterine release system (IUD); the release rate of the active compound(s) is selected in this case so that the dose released daily lies within the dosage ranges that are already indicated.

It is also possible to incorporate the substances according to the invention in a transdermal system and thus to administer them transdermally.

The starting compounds first required for the production of the compounds of general formula (I) are available according to the synthesis route below:

Diagram 1:

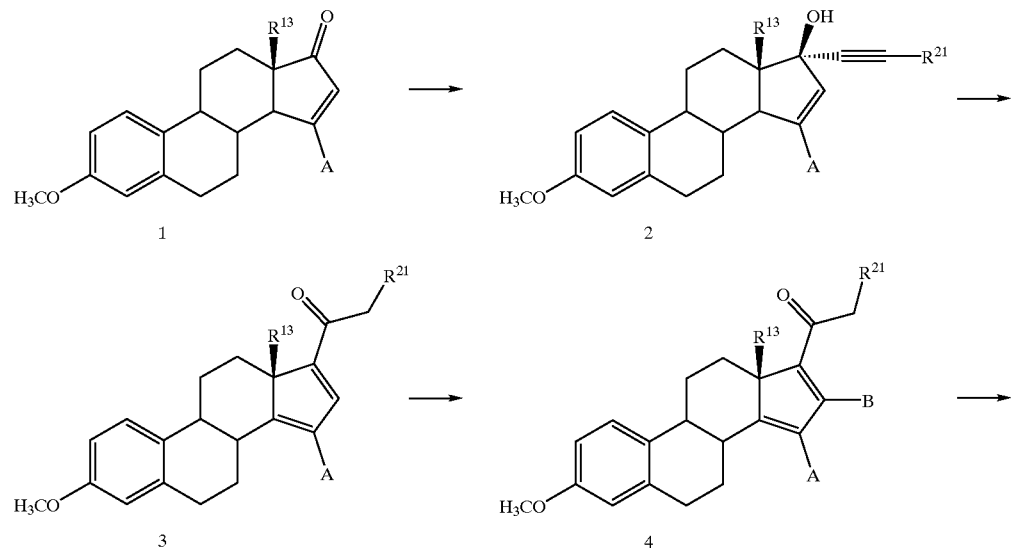

-continued

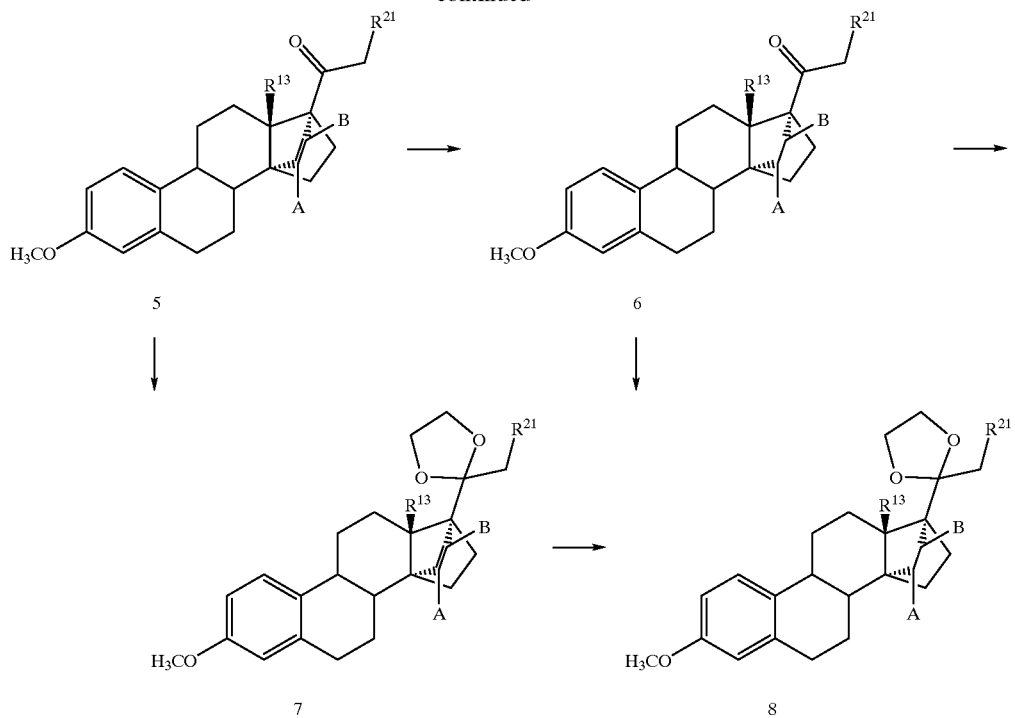

$R^{13}$=—CH$_3$, —C$_2$H$_5$; $R^{21}$=hydrogen, C$_1$–C$_3$ alkyl; A and B=independently of one another, hydrogen or C$_1$–C$_3$ alkyl.

According to diagram 1, for example, a compound of general formula 1 that is known in the art (see, for example, DE 43 26 240 A1) can be converted by addition of the anion of a terminal alkine to a compound of general formula 2 that is known in the art. The latter is converted by reaction with an acid such as, for example, sulfuric acid, hydrochloric acid, p-toluenesulfonic acid, formic acid or acetic acid in the presence or absence of inert solvents, such as, for example, toluene, tetrahydrofuran or dichloromethane, to a compound of general formula 3 (see, for example, D. K. Phillips, P. P. Wickham, G. O. Potts and A. Arnold, J. Med. Chem., 11, 924 (1968)). If desired, a compound of general formula 3 can be converted with suitable nucleophiles, for example dialkyl copper compounds, followed by an oxidation, for example a modified Saegusa oxidation (cf. I. Minami et al., Tetrahedron 42, 2971 (1986) or EP-A 0299913) to a compound of general formula 4, and B then stands for an alkyl radical. Otherwise B stands for hydrogen. The compound of general formula 4 can then be converted with ethene under pressure and at elevated temperature according to processes known in the art in a cycloaddition to a compound of general formula 5. The latter can then be converted according to standard processes by hydrogenation of the $17^1,17^2$-double bond (carbon atom $17^1$ or $17^2$ designates the carbon atom, on which substituent $R^{17^1}$ or $R^{17^2}$ is located) with noble metal catalysts, such as, for example, platinum or palladium, to a compound of general formula 6. The compounds of general formulas 5 and 6, in which $R^{21}$ stands for a hydrogen atom, can also be alkylated according to standard processes, and are converted to the corresponding compounds of general formulas 5 and 6, in which $R^{21}$ stands for a C$_1$–C$_3$ alkyl group (see, for example, R. Bloch Tetrahedron 39, 639 (1983)). The compounds of general formula 5 can be ketalized according to standard methods to compounds of general formula 7, which can be converted by hydrogenation to the compounds of general formula 8. These compounds can also be obtained by the ketalization of the compound of general formula 6. In this case, instead of the 1,2-ethanediylbis(oxy) protective group on carbon atom 20, generally also other known keto protective groups, such as, for example, the 2,2-dimethyl-1,3-propanediylbis(oxy) group, are suitable according to the invention. Other protective groups, which can be used within the scope of this invention, can be found in "Protective Groups in Organic Synthesis," Theodora W. Greene, Peter G. N. Wuts, John Wiley and Sons, Inc., New York, 1991, pp. 178–210.

The compounds of general formulas 5 and 6, in which $R^{13}$ means an ethyl group and $R^{21}$ means a hydrogen atom or a C$_1$–C$_3$ alkyl group or $R^{13}$ means a methyl group and $R^{21}$ means a C$_1$–C$_3$ alkyl group belong overall as intermediate compounds of general formula II to the object of this invention:

(II)

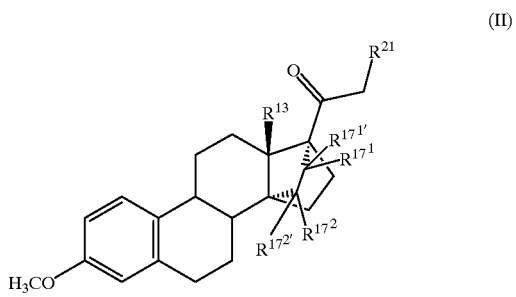

in which
$R^{13}$=—C$_2$H$_5$; $R^{21}$=hydrogen, C$_1$–C$_3$ alkyl or
$R^{13}$=—CH$_3$; $R^{21}$=C$_1$–C$_3$ alkyl and
$R^{17^1}$ and $R^{17^2}$=independently of one another, hydrogen or C$_1$–C$_3$ alkyl,
$R^{17^{1'}}$ and $R^{17^{2'}}$=in each case hydrogen or together a bond.

The compounds of general formulas 7 and 8 that are obtained by ketalization of the compounds of general formula 5 or 6 are all new and belong overall as intermediate compounds of general formula III also to the object of this invention:

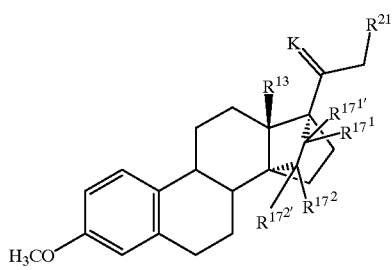
(III)

in which $R^{13}$=—$CH_3$, —$C_2H_5$, $R^{17^1}$ and $R^{17^2}$=independently of one another, hydrogen or $C_1$–$C_3$ alkyl, $R^{17^{1'}}$ and $R^{17^{2'}}$=in each case hydrogen or together a bond, K=a ketal protective group, $R^{21}$=hydrogen, $C_1$–$C_3$ alkyl.

Diagram 2

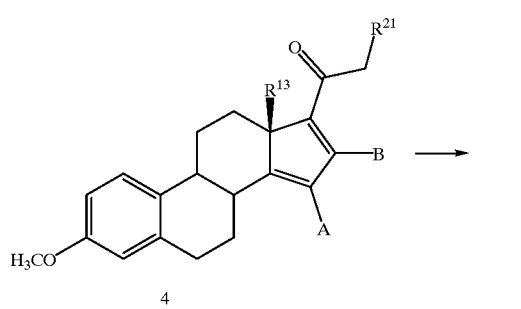
4

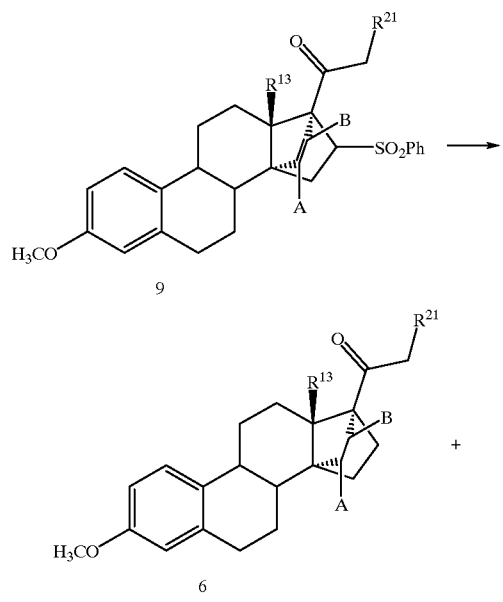
9

6

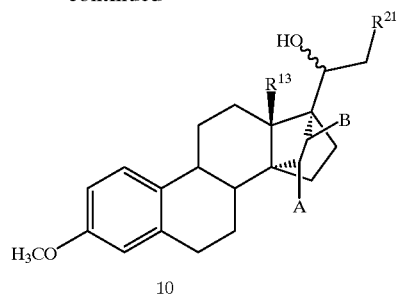
10

$R^{13}$=—$CH_3$, —$C_2H_5$; $R^{21}$=hydrogen, $C_1$–$C_3$ alkyl; A and B=independently of one another, hydrogen or $C_1$–$C_3$ alkyl.

According to diagram 2, the reaction of a compound of general formula 4 is also possible according to processes known in the art with phenyl vinyl sulfone in inert solvents to a compound of general formula 9 (J. R. Bull and R. I. Thompson S. Afr. J. Chem. 44, 87 (1991)). The reduction of this compound by metals such as Raney nickel or magnesium in lower alcohols such as methanol or ethanol results in compounds of general formulas 6 and 10, which can be converted to one another by oxidation/reduction processes, for example, with pyridinium dichromate or under the conditions of an Oppenauer oxidation or with sodium borohydride or lithium aluminum hydride.

The production of the compounds according to the invention, which are substituted in 15- and/or 16-positions, is carried out by the reaction of a compound of general formula 4 with suitable olefins, such as, for example, propene, 2-methylpropene, 2-butene, cyclopentene, cyclohexene or 2,5-dihydrofuran and optionally the hydrogenation of the $17^1$, $17^2$-double bond that is produced. The additional reactions of the compounds thus obtained are carried out analogously to the additional reactions of the compounds of general formula 6.

For the production of the compounds according to the invention, which carry an alkyl or alkenyl radical in 16-position, a compound of general formula 4 can also be reacted with an acrylic acid ester of formula $H_2C$=CH—COOalkyl (alkyl=$C_1$–$C_4$ alkyl) according to diagram 3.

Diagram 3

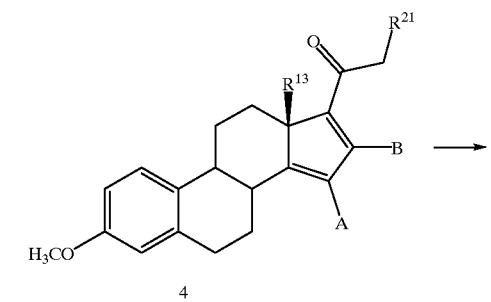
4

-continued

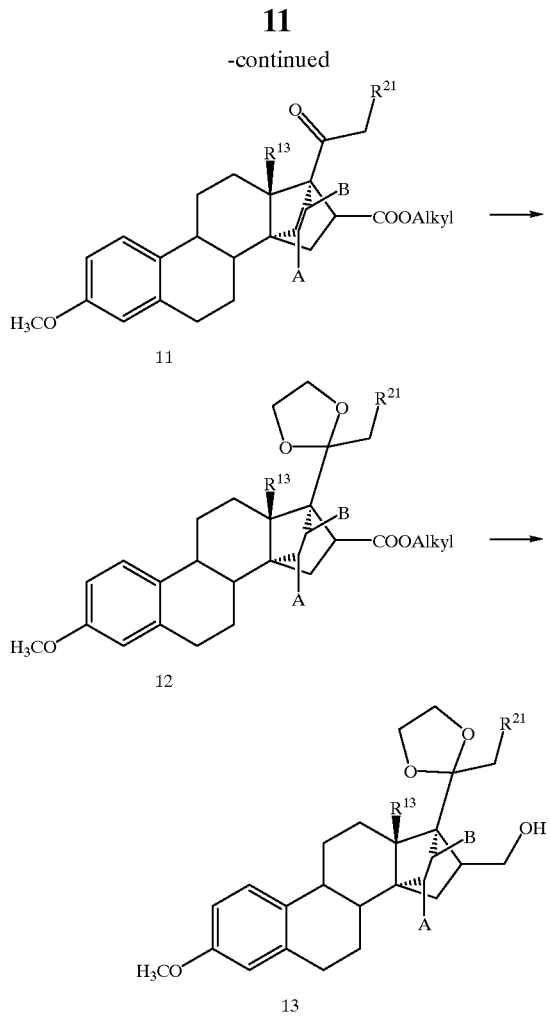

$R^{13}$=—$CH_3$, —$C_2H_5$; $R^{21}$=hydrogen, $C_1$–$C_3$ alkyl; A and B=independently of one another, hydrogen or $C_1$–$C_3$ alkyl After ketalization of the 20-keto group and hydrogenation of the $17^1,17^2$-double bond that is produced, the compounds of general formula 11 thus obtained are reacted to the compounds of general formula 12, which can be converted with lithium aluminum hydride to the 16-hydroxymethyl compounds of general formula 13.

According to standard processes (see, for example, J. Hooz and S. S. Gilani, Can. J. Chem. 46, 86 (1968)), the compounds of general formula 13 can be converted to the corresponding 16-bromomethyl compounds, which are reduced to the 16-methyl compounds under the conditions of a Birch reduction. In this case, the aromatic A-ring is also reduced while forming the 2,5(10)-diene structure.

The compounds of general formula 13 can be converted by oxidation according to processes known in the art, for example, with pyridinium dichromate, to the corresponding 16-aldehydes, which, after reaction with corresponding phosphorylidene, result in the 16-alkenyl compounds according to the invention, which can be converted by hydrogenation to 16-alkyl compounds.

By heating with aryl hydrazines according to processes known in the art (cf., for example, M. Pieper et al., Liebigs Ann. Chem., 1334 (1986)), 16-aldehydes can be converted to aryl hydrazones, which fragment into 16-exomethylene compounds in the case of base treatment in terms of a Shapiro or Bamford-Stevens reaction. As an alternative, the 16-aldehydes can be converted by reaction with sulfonic acid derivatives, such as, for example, sulfonic acid halides or sulfonic anhydrides in the presence of bases, such as, for example, lithium diisopropylamide or else potassium hexamethyl disilazide in inert solvents, such as, e.g., tetrahydrofuran, to the enolsulfonic acid esters, which by reductive cleavage, for example, by treatment with ammonium formate in the presence of catalytic amounts of a palladium(II) catalyst, such as, for example, palladium(II) acetate in suitable solvents, for example, acetonitrile, change into the 16-exomethylene compound.

The compounds of general formulas 11, 12 and 13 together with the derivatives described in the text are all new and belong as intermediate compounds of general formula IV to the object of this invention:

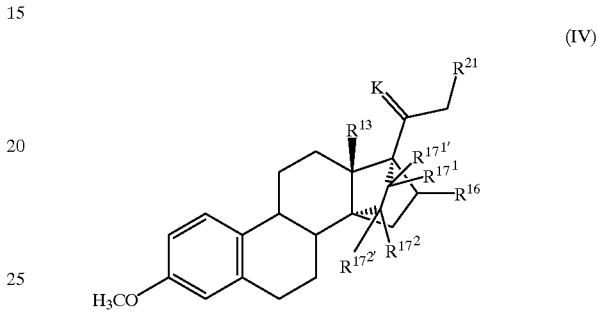

in which
$R^{13}$=$CH_3$, —$C_2H_5$,
$R^{16}$=—COOalkyl, in which alkyl is a $C_1$–$C_4$ alkyl radical, or —$CH_2OH$ or CHO, or methylene,
$R^{17^1}$ and $R^{17^2}$=independently of one another, hydrogen or $C_1$–$C_3$ alkyl,
$R^{17^{1'}}$ and $R^{17^{2'}}$=in each case hydrogen or together a bond,
K=an oxygen atom or a ketal protective group,
$R^{21}$=hydrogen, $C_1$–$C_3$ alkyl.

The compounds of general formula 12 can be converted by alkaline hydrolysis to the corresponding carboxylic acids, which by decarboxylation and oxidation, for example, by heating with lead tetraacetate and copper(II) acetate in toluene (see, for example, J. D. Bacha and J. K. Kochi, Tetrahedron 24, 2215 (1968)) result in derivatives with a 15,16-double bond. 14,17-$C_2$-bridged derivatives with a 15,16-double bond are also available in other ways:

1. The reaction of a compound of general formula 4 with maleic anhydride to the Diels-Alder product, followed by catalytic hydrogenation of the $17^1$, $17^2$-double bond and after heating with bis(triphenylphosphine)nickel dicarbonyl in suitable solvents such as diglymes, yields the corresponding 15,16-double bond derivative (see, for example, K. Wiesner et al., Can. J. Chem. 52, 640 (1974)). As an alternative, it can be reacted starting from $17^1,17^2$-saturated anhydride with bases, such as, for example, aqueous sodium hydroxide solution, to 15,16-dicarboxylic acid, which is converted via double decarboxylation to the corresponding 15,16-double bond derivative (see, for example, C. M. Cimarusti and J. Wolinsky, J. Am. Chem. Soc. 90, 113 (1968)). For example, the dicarboxylic acid is heated with lead tetraacetate in suitable solvents, for example, pyridine, to temperatures of 30–100° C.

The Diels-Alder adduct can also be used for the synthesis of other derivatives: reduction of the Diels-Alder product to lactone with suitable reducing agents, such as, for example, sodium borohydride (see, for example, D. M. Bailey and R. F. Johnson, J. Org. Chem. 35, 3574 (1970)), oxidation of the 20-alcohol that is produced, for example, with pyridinium chlorochromate and protection of the ketone as ketal results, after reduction of lactone with suitable reducing agents, such as, for example, lithium aluminum hydride, to the 15,16-bishydroxymethyl compound. The hydroxy functions can be condensed, for example, under suitable conditions to a cyclic ether. This is preferably carried out under basic conditions, such as, for example, by treatment with sulfonic acid derivatives, such as sulfonic acid halides or sulfonic anhydrides in the presence of bases, such as, for example, pyridine.

2. The reaction of a compound of general formula 4 with vinylene carbonate (in Diels-Alder reactions with vinylene carbonate, see, for example, Y. Shizuri et al., J. Chem. Soc., Chem. Commun. 292 (1985) or G. H. Posner et al., Tetrahedron Lett. 32, 5295 (1991)) in terms of a Diels-Alder reaction according to diagram 4 results in a cycloaddition product of formula 14. After hydrogenation of the $17^1,17^2$-double bond and cleavage of the cyclic carbonate according to standard processes, such as, for example, the reaction of the carbonate in a suitable solvent, such as, e.g., methanol with a base, such as, e.g., potassium carbonate, a diol of formula 17 is obtained. The sequence of hydrogenation and carbonate cleavage can be done in any order.

Diagram 4

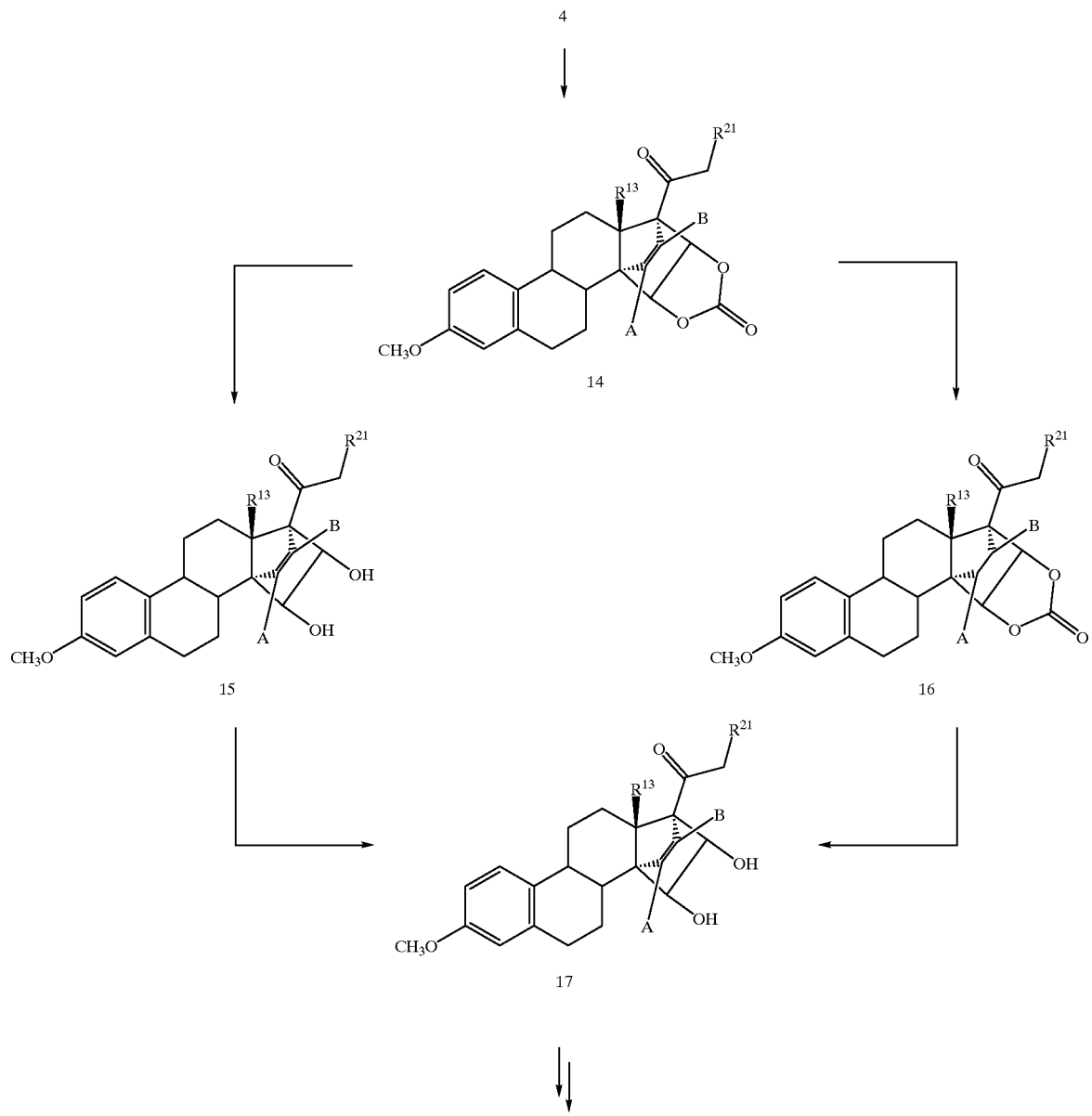

-continued

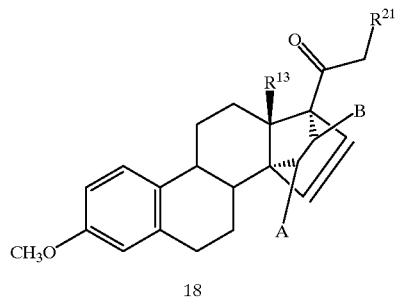

18

$R^{13}$=—$CH_3$, —$C_2H_5$; $R^{21}$=hydrogen, $C_1$–$C_3$ alkyl; A and B=independently of one another, hydrogen or $C_1$–$C_3$ alkyl.

For conversion of vicinal diols to olefins, a whole series of methods that are familiar to one skilled in the art are available to choose from (cf., for example, M. Ando et al., Chemistry Letters 879 (1986)). For example, a diol of general formula 17 can be reacted with an orthoester, such as, for example, trimethyl orthoformate with acid catalysis, for example, with pyridinium paratoluenesulfonate, in a suitable solvent, here dichloromethane can be mentioned as an example, or without a solvent to the corresponding orthoester, which when heating in suitable solvents, such as, e.g., acetic anhydride, fragments into an olefin of general formula 18.

The compounds of general formulas 14, 15, 16, 17 and 18 together with the derivatives described in the text are all new and belong as intermediate compounds of general formula V to the object of this invention:

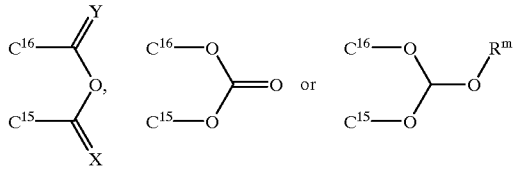

(V)

in which
$R^{13}$=—$CH_3$, —$C_2H_5$,
$R^{15}$ and $R^{16}$=together a ring of partial formulas in which
X and Y=independently of one another, in each case an oxygen atom or two hydrogen atoms and
$R^m$=$C_1$–$C_3$ alkyl
or
$R^{15}$ and $R^{16}$=each per se for an —OH group or
$R^{15}$ and $R^{16}$=together a bond
and
$R^{17^1}$ and $R^{17^2}$=independently of one another, hydrogen or $C_1$–$C_3$ alkyl,
$R^{17^{1'}}$ and $R^{17^{2'}}$=in each case hydrogen or together a bond,
K=an oxygen atom or a ketal protective group,
$R^{21}$=hydrogen or $C_1$–$C_3$ alkyl.

Other substitution patterns on the D-ring of 14,17-$C_2$-bridged steroids can be produced, e.g., starting from the Diels-Alder products of formula 19, which can be produced by reaction of a diene of general formula 4 with an acetylene carboxylic acid alkyl ester (alkyl=$C_1$–$C_4$ alkyl):

Diagram 5

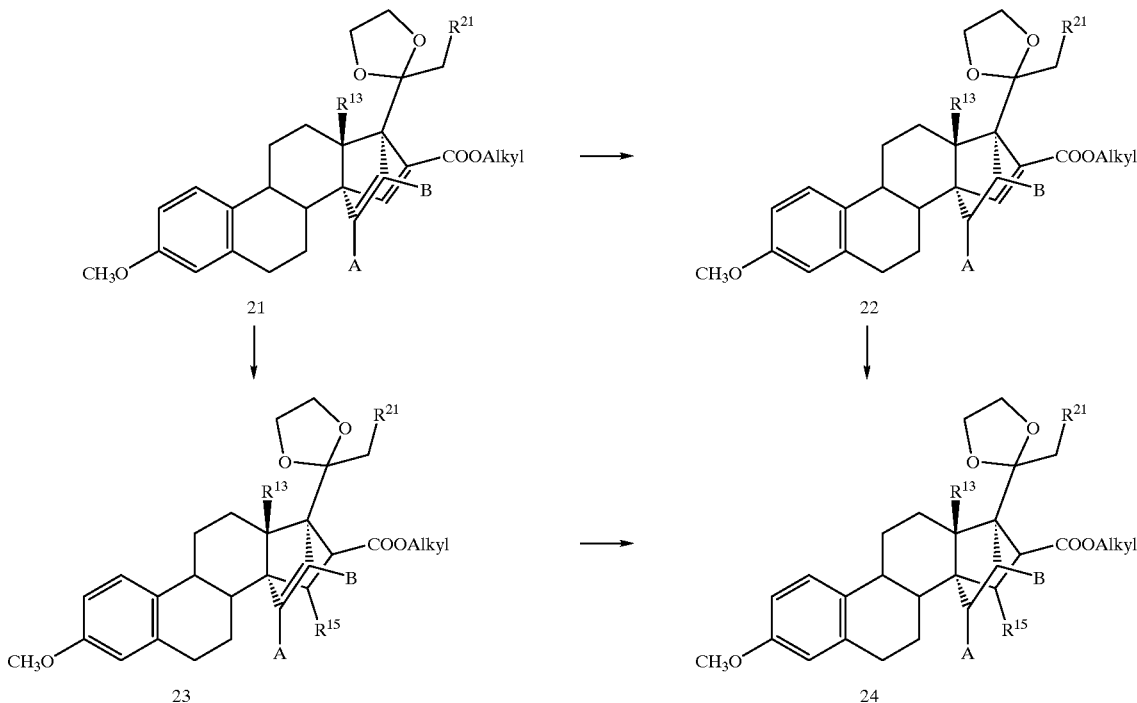

$R^{13}$=—$CH_3$, —$C_2H_5$; $R^{21}$=hydrogen, $C_1$–$C_3$ alkyl; A and B=independently of one another, hydrogen or $C_1$–$C_3$ alkyl;

$R^{15}$=hydrogen, $C_1$–$C_3$ alkyl.

Ketalization of cycloaddition product 19 yields a compound of general formula 21. The selective reduction of the 15,16-double bond is possible with magnesium in a suitable solvent, preferably an alcohol, such as, for example, methanol, and yields a compound of formula 23, in which $R^{15}$ then means a hydrogen atom. 1,4-Additions to compounds of formula 21 are carried out according to methods known in the art. Thus, for example, the reaction with dimethyl copper in suitable solvents, such as, for example, tetrahydrofuran, yields a compound of general formula 23, in which $R^{15}$ then means a methyl group. By catalytic hydrogenation of noble metal catalysts, if necessary, the $17^1$, $17^2$-double bond can be removed selectively in any intermediate stage. The ester function on $C^{16}$ can be modified in varied ways. In addition to the possibilities already described for the follow-on chemistry of cycloaddition with acrylic acid alkyl esters, the following can be mentioned here:

After reduction with lithium aluminum hydride, conversion of the alcohol that is produced to a leaving group, such as, for example, a sulfonic acid ester, which is obtained, e.g., by reaction with a sulfonic halide with use of suitable bases, such as, for example, pyridine with or without the aid of an inert solvent, such as, for example, dichloromethane, and subsequent reduction with suitable reducing agents, for example, lithium triethylborohydride, α,β-saturated esters, such as, for example, compounds of general formulas 23 and 24, yield 16-methyl derivatives.

In the case of treatment with suitable reducing agents, such as, for example, diisobutylaluminum hydride, optionally with the aid of Lewis acids, for example, zinc chloride, α,β-unsaturated esters, such as, for example, compounds of general formulas 21 and 22, yield 15,16-unsaturated 16-hydroxymethyl derivatives. The conversion to the corresponding carboxylic acid ester or sulfonic acid ester is possible according to methods known in the art. For example, allyl alcohol is reacted with acetyl chloride in pyridine to the corresponding acetic acid ester. Under the conditions of a Birch reduction, the corresponding 15,16-unsaturated 16-methyl derivative is then obtained (for Birch reduction of allylacetates, cf., for example, R. T. Jacobs et al., J. Org. Chem. 55, 4051 (1990)). In this case, the aromatic A-ring is also reduced while forming the 2,5(10)-diene structure.

The compounds of general formulas 19, 20, 21, 22, 23 and 24 together with the derivatives described in the text are all new and belong as intermediate compounds of general formula VI to the object of this invention:

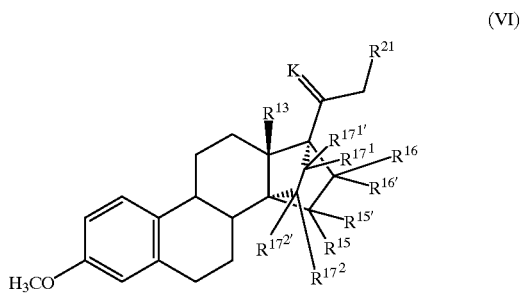

(VI)

in which $R^{13}$=—$CH_3$, —$C_2H_5$, $R^{15}$ and $R^{16}$=in each case hydrogen or together a bond, $R^{15'}$=hydrogen or $C_1$–$C_3$ alkyl, $R^{16'}$=—COOalkyl, in which alkyl is a $C_1$–$C_4$ alkyl radical, or $CH_2OH$ or CHO or a $C_1$–$C_3$ alkyl radical, $R^{17^1}$ and $R^{17^2}$=independently of one another, hydrogen or $C_1$–$C_3$ alkyl, $R^{17'}$ and $R^{17''}$=in each case hydrogen or together a bond,
K=an oxygen atom or a ketal protective group,
$R^{21}$=hydrogen or $C_1$–$C_3$ alkyl.

In the compounds of general formulas III, IV, V and VI above, K, if this is a ketal protective group, preferably stands for a 1,2-ethanediylbis(oxy) or 2,2-dimethyl-1,3-propanediylbis(oxy) group.

Under the conditions of a Birch reduction known in the art (see, for example, J. Fried, J. A. Edwards, Organic Reactions in Steroid Chemistry, von Nostrand Reinhold Company 1972, pp. 1–60), the reduction of the compounds of general formulas 6, 7, 8 and 9 thus obtained and the corresponding derivatives, which are substituted in 15-, 16-, $17^1$- or $17^2$- positions, results in the corresponding 3-methoxy-Δ-2,Δ5 (10) derivatives. The latter can be reacted by reaction with diluted mineral acids and optionally a subsequent oxidation of the 20-hydroxy group according to standard processes, such as, for example, with pyridinium dichromate, to the Δ4-3-ketones of general formula (I) according to the invention. The 3-methoxy-Δ2,Δ5(10) derivatives can also be reacted, however, according to standard processes (see, for example, D. Burn and V. Petrow J. Chem. Soc., 364 (1962)) to Δ5(10)-3-ketones, which can be converted by a bromation-dehydrobromation and optionally a subsequent oxidation of the 20-hydroxy group to the Δ4,Δ9-3-ketones of general formula (I) according to the invention (see, for example, J. Fried, J. A. Edwards, Organic Reactions in Steroid Chemistry, von Nostrand Reinhold Company 1972, pp. 265–374). According to standard processes, ketalization of the Δ4,Δ9-3-ketones results in Δ5(10),Δ9(11)-3-ketals, which can be cleaved under mild acid conditions, for example, with aqueous acetic acid, to the Δ5(10),Δ9(11)-3-ketones. The deconjugation of the Δ4,Δ9-3-ketones can optionally also be carried out by treatment with acids, for example, aqueous hydrochloric acid with the addition of a solubilizer, such as, for example, acetone. After removal of optionally still present protective groups, the reaction of the deconjugated dienones that are obtained with oxidizing agents (cf., for example, DE 2748250 C2), such as, for example, 2,3-dichloro-5,6-dicyano-p-benzoquinone in suitable solvents, for example, dichloromethane, results in the Δ4,Δ9,Δ11-3-ketones of general formula (I) according to the invention.

The next steps normally apply to the creation of radicals $R^6$, $R^{6'}$ and $R^7$. The introduction of a 6,7-double bond is possible via a dienol ether bromation and subsequent hydrogen bromide cleavage (see, for example, J. Fried, J. A. Edwards, Organic Reactions in Steroid Chemistry, von Nostrand Reinhold Company 1972, pp. 265–374) or else by reaction with chloranil or 2,3-dichloro-5,6-dicyano-p-benzoquinone.

The dienol ether bromation can be carried out, for example, analogously to the instructions in Steroids I, 233 (1965). The hydrogen bromide cleavage is possible by heating the 6-bromine compound with basic agents, such as, for example, lithium bromide or lithium carbonate in aprotic solvents such as dimethylformamide at temperatures of 50–150° C. or else by the 6-bromine compounds being heated in collidine or lutidine.

For compounds with a 6,7-methylene function, the introduction is also carried out from the dienone by reaction with dimethylsulfoxonium methylide, but here a mixture of α- and β-isomers occurs (the ratio depends on the substrates used and is approximately 1:1), which can be separated, for example, via column chromatography.

Compounds with $R^7$ equals alkyl are produced from 4,6-dien-3-one compounds by 1,6-addition according to known methods (J. Fried, J. A. Edwards: Organic Reactions in Steroid Chemistry, von Nostrand Reinhold Company 1972, pages 75–82; A. Hosomi and H. Sakurai, J. Am. Chem. Soc. 99, 1673 (1977)). The introduction of 7-alkyl functions is carried out in this connection generally via dialkyl copper lithium compounds.

Compounds in which $R^6$ represents a chlorine atom and $R^{6'}$ and $R^7$ form a common additional bond are also represented starting from the 4,6-dien-3-one compounds. In this connection, first the 6,7-double bond is epoxidated with use of organic peracids, such as, for example, meta-chloroperbenzoic acid in methylene chloride, optionally in the presence of sodium bicarbonate solution (see W. Adam, J. -C. Liu and O. Rodriguez, J. Org. Chem. 38, 2269 (1973)). The opening of this epoxide and the elimination of the primarily formed 7α-hydroxy group is carried out, for example, by reaction with hydrochloric gas in glacial acetic acid (see, i.a., DE-A 11 58 966 and DE-A 40 06 165).

The introduction of a 6-methylene group can be carried out, for example, starting from a 3-amino-3,5-diene derivative by reaction with formalin in alcoholic solutions with the formation of a 6α-hydroxymethyl group and subsequent acid dehydration, for example, with hydrochloric acid in dioxane/water. The dehydration can also be carried out, however, in the way that first a leaving group is introduced and then eliminated. As leaving groups, for example, mesylate, tosylate or benzoate are suitable (see DE-A 34 02 329, EP-A 150157, U.S. Pat. No. 4,584,288(86); K. Nickisch, S. Beier, D. Bittler, W. Elger, H. Laurent, W. Losert, Y. Nishino, E. Schillinger and R. Wiechert, J. Med. Chem. 34, 2464 (1991)).

Another possibility for the production of 6-methylene compounds consists in the direct reaction of 4(5) unsaturated 3-ketones with acetals of formaldehyde in the presence of sodium acetate with, for example, phosphorus oxychloride or phosphorus pentachloride in suitable solvents such as chloroform (see, for example, K. Annen, H. Hofmeister, H. Lautrent and R. Wiechert, Synthesis 34, (1982)). An additional possibility for the introduction of the 6-methylene group consists in the reaction of a Δ4-3-ketone to a dienol ether, its reaction with dimethylformamide and phosphorus oxychloride to aldehyde and its reduction with complex borohydrides and subsequent dehydration with mineral acids according to processes known in the art (see WO 90/12027).

The 6-methylene compounds can be used for the production of the compounds of general formula (I), in which $R^6$ equals methyl and $R^{6'}$ and $R^7$ form a common additional bond.

In this connection, for example, a process described by D. Burn, D. N. Kirk and V. Petrow in Tetrahedron 21, 1619 (1965) can be used, in which an isomerization of the double bond is achieved by heating the 6-methylene compounds in ethanol with 5% palladium-carbon as catalyst, which was pretreated either with hydrogen or by heating with a small amount of cyclohexene. The isomerization can also be carried out with a non-pretreated catalyst, if a small amount of cyclohexene is added to the reaction mixture. The occurrence of small portions of hydrogenated products can be prevented by the addition of an excess of sodium acetate.

The production of 6-methyl-4,6-dien-3-one derivatives can also be carried out directly, however (see K. Annen, H. Hofmeister, H. Laurent and R. Wiechert, Liebigs Ann. Chem. 712, (1983)).

Compounds, in which $R^6$ represents an α-methyl function, can be produced from the 6-methylene compounds by hydrogenation under suitable conditions. The best results (selective hydrogenation of the exo-methylene function) are achieved by transfer-hydrogenation (E. A. Brande, R. P. Linstead and P. W. D. Mitchell, J. Chem. Soc. 3578 (1954)). If the 6-methylene derivatives are heated in a suitable solvent, such as, for example, ethanol, in the presence of a hydride donor, such as, for example, cyclohexene, and a noble metal catalyst, for example, platinum or palladium, very good yields of 6α-methyl derivatives are thus obtained. Small portions of 6β-methyl compounds can be acidically isomerized (see, for example, D. Burn, D. N. Kirk and V. Petrow, Tetrahedron 21, 1619 (1965)).

The alkylation of 17-acetyl derivatives to homologous ketones can be carried out not only, as already described, on compounds with an aromatic A-ring, but also in the further course of the synthesis on suitably protected derivatives.

The introduction of a 21-OH substituent is carried out on suitably protected 20-keto compounds according to processes known in the art, such as the direct oxidation of an enolate (see, for example, E. Vedejs, D. A. Engler and J. E. Teischow, J. Org. Chem. 43, 188 (1978) and J. C. Anderson and S. C. Smith, Synlett 1990, 107) or the reaction of enolate to the corresponding iodide, substitution of the iodide by acetate and hydrolysis of the acetate. The diastereomeric mixtures that are optionally produced in this case can be separated by chromatography.

After introduction of all radicals, protective groups that are still present are cleaved according to standard processes.

The compounds of general formula (I) that are obtained with $R^3$ equals oxygen can optionally be converted by reaction with hydroxylamine hydrochloride in the presence of tert-amines at temperatures between −20 and +40° C. to oximes (general formula (I) with $R^3$ meaning N—OH, and the hydroxy group can be in syn or anti position).

The removal of the 3-oxo group to an end product of general formula (I) with $R^3$ meaning two hydrogen atoms can be carried out, for example, according to the instructions indicated in DE-A-2805490 by reductive cleavage of the thioketal.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 44 47 406.1, filed Dec. 23, 1994, are hereby incorporated by reference.

The examples below are used for a more detailed explanation of the invention.

EXAMPLES

Example 1

14,17-Etheno-19-norpregn-4-ene-3,20-dione a) 3-Methoxy-19-norpregna-1,3,5 (10),14,16-pentaen-20-one 84.2 g of 3-methoxy-19-nor-17α-pregna-1,3,5(10),15-tetraen-20-in-17β-ol (J. Med. Chem., 11, 924 (1968)) is heated to 110° C. in 875 ml of 86% formic acid with stirring. After 2 hours, it is allowed to cool with the addition of 1000 ml of water. The precipitated solid is filtered out, dried and chromatographed on silica gel with a mixture of ethyl acetate and hexane. 47.8 g of 1a) is obtained.

Flash point: 152–155° C.

$^1$H-NMR (CDCl$_3$): δ=1.22 ppm (s,3H,H-18); 2.35 (s,3H, H-21); 3.78 (s,3H,3-OCH$_3$); 6.08 (m,1H,H-15); 6.68 (d,J=3 Hz, 1H,H-4); 6.74 (dd,J=9, 3 Hz,1H,H-2); 7.23 (d,J=9 Hz,1H,H-1); 7.27 (d,J=3 Hz,1H,H-16).

b) 3-Methoxy-14,17-etheno-19-norpregna-1,3,5(10)-trien-20-one

A solution of 200 g of the substance, described under 1a), in 2.5 l of benzene is heated to 160° C. under an ethylene pressure of 300 bar for 240 hours. After cooling, the reaction mixture is concentrated by evaporation, and the residue is chromatographed on silica gel with a mixture of ethyl acetate and hexane. 175 g of 1b) is obtained.

$^1$H-NMR (CDCl$_3$): d=0.91 ppm (s,3H,H-18); 2.22 (s,3H, H-21); 3.78 (s,3H,3-OCH$_3$); 6.07 and 6.14 (2d,J=6 Hz, 1H, H-17$^1$ and H-17$^2$ each); 6.65 (d,J=3 Hz,1H,H-4); 6.73 (dd,J=9, 3 Hz,1H,H-2); 7.22 (d,J=9 Hz,1H,H-1).

c) 20,20-[1,2-Ethanediylbis(oxy)]-3-methoxy-14,17-etheno-19-norpregna-1,3,5(10)-triene 75 ml of ethylene glycol, 63 ml of trimethyl orthoformate and 1.25 g of p-toluenesulfonic acid are added to a solution of 25 g of the compound, described under 1b), in 175 ml of dichloromethane at room temperature with stirring. After 90 minutes, 15 ml of triethylamine and 100 ml of dichloromethane are added, and the reaction mixture is washed three times with concentrated sodium bicarbonate solution. The organic phase is dried on potassium carbonate, filtered out and concentrated by evaporation. 31 g of 1c) is obtained.

$^1$H-NMR (CDCl$_3$): δ=0.98 ppm (s,3H,H-18); 1.37 (s,3H, H-21); 3.78 (s,3H,3-OCH$_3$); 3.95–4.05 (m,4H,20-OCH$_2$CH$_2$O—); 5.97 and 6.01 (2d,J=6 Hz, 1H,H-17$^1$ and H-17$^2$ each); 6.65 (d,J=3 Hz,1H,H-4); 6.72 (dd,J=9, 3 Hz,1H,H-2); 7.22 (d,J=9 Hz,1H,H-1).

d) 20,20-[1,2-Ethanediylbis(oxy)]-3-methoxy-14,17-etheno-19-norpregna-2,5(10)-diene A solution of 31 g of the compound, described under 1c), in a mixture of 400 ml of tetrahydrofuran and 70 ml of tert-butanol is added to 2.2 l of liquid ammonia at −70° C. 16 g of lithium is added in portions to this mixture with stirring. It is allowed to heat to −40° C., 350 ml of ethanol is instilled after 5.5 hours, the mixture is then allowed to heat to room temperature, diluted with water and extracted with ethyl acetate. The organic phase is washed with water and concentrated sodium chloride solution, dried on sodium sulfate, filtered out and concentrated by evaporation in a vacuum. 23.1 g of crystalline 1d) is obtained, which is reacted in the next steps without further purification.

$^1$H-NMR (CDCl$_3$): d=0.96 ppm (s,3H,H-18); 1.33 (s,3H, H-21); 3.55 (s,3H,3-OCH$_3$); 3.88–4.03 (m,4H,20-OCH$_2$CH$_2$O—); 4.63–4.67 (m,1H,H-2); 5.93 and 6.07 (2d, J=6 Hz, 1H,H-17$^1$ and H-17$^2$ each).

e) 14,17-Etheno-19-norpregn-4-ene-3,20-dione

A solution of 2.7 g of the compound, described under 1d), in 30 ml of tetrahydrofuran and 150 ml of acetone are mixed with stirring with 7.8 ml of 4N hydrochloric acid. After 2 hours, the solvent is removed, and the residue is recrystallized from diisopropyl ether. 1.72 g of 1e) is obtained.

Flash point: 139–143° C.

$^1$H-NMR (CDCl$_3$): δ=0.92 ppm (s,3H,H-18); 2.18 (s,3H, H-21); 5.88 (s broad,1H,H-4); 6.04 (s,2H,H-17$^1$ and H-17$^2$).

Example 2

14,17-Etheno-19-norpregna-4,6-diene-3,20-dione a) 3-Ethoxy-14,17-etheno-19-norpregna-3,5-dien-20-one 6.1 ml of ethanol, 6.1 ml of triethyl orthoformate and 145 mg of p-toluenesulfonic acid are added to a solution of 2.02 g of the compound, described under 1e), in 80 ml of tetrahydrofuran with stirring. After 2 hours at room temperature, 2.5 ml of triethylamine is added, diluted with sodium bicarbonate solution and the mixture is extracted with ethyl acetate. The organic phase is washed with water and concentrated sodium chloride solution, dried on sodium sulfate, filtered out and concentrated by evaporation. 3.3 g of 2a) is obtained as colorless oil, which is reacted in the next step without further purification.

b) 14,17-Etheno-19-norpregna-4,6-diene-3,20-dione

A solution of 3.3 g of the compound, described under 2a), in 41 ml of dioxane and 10 ml of water is mixed with 16 ml of a 10% sodium acetate solution and then at 0° C. with stirring with 890 mg of 1,3-dibromo-5,5-dimethylhydantoin. After 15 minutes, the reaction mixture is poured on ice water and extracted with ethyl acetate. The organic phase is washed with concentrated sodium chloride solution, dried on sodium sulfate and filtered in a suspension from 2.4 g of lithium carbonate and 3.4 g of lithium bromide in 120 ml of dimethylformamide. The mixture is heated to 150° C. while ethyl acetate is distilled off. After one hour, it is allowed to cool, the reaction mixture is diluted with water and extracted with ethyl acetate. The organic phase is washed with water and concentrated sodium chloride solution, dried on sodium sulfate, filtered out and concentrated by evaporation. The residue is chromatographed on silica gel with a mixture of n-hexane and ethyl acetate. 880 mg of 2b) is obtained.

Flash point: 150–152° C. $[\alpha]_D^{20}$=+172.3° (CHCl$_3$; c=0.510).

$^1$H-NMR (CDCl$_3$): d=0.95 ppm (s,3H,H-18); 2.19 (s,3H, H-21); 5.82 (s broad,1H,H-4); 5.92 and 6.04 (2d,J=6 Hz, 1H,H-17$^1$ and H-17$^2$ each); 6.20–6.32 (m,2H,H-6 and H-7).

Example 3

7β-Methyl-14,17-etheno-19-norpregn-4-ene-3,20-dione

A suspension of 1.9 g of copper(I) iodide in 25 ml of diethyl ether is mixed at 0° C. drop by drop with 8.5 ml of a 1.6 molar solution of methyllithium in diethyl ether. After 30 minutes of stirring at 0° C., 40 ml of tetrahydrofuran is added and then at −40° C., 1.23 ml of boron trifluoride etherate and then a solution of 340 mg of the compound, described under 2b) in 15 ml of tetrahydrofuran is instilled. It is allowed to heat within 4 hours to room temperature, stirred for 72 more hours and the reaction mixture is poured into 100 ml of concentrated ammonium chloride solution. The mixture is extracted four times with ethyl acetate, the combined organic phases are washed with water, dried on sodium sulfate, filtered out and concentrated by evaporation. After chromatography on silica gel with a mixture of ethyl acetate and hexane, 46 mg of 3) is obtained.

Flash point: 133–135° C.

$^1$H-NMR (CDCl$_3$): d=0.94 ppm (s,3H,H-18); 1.07 (d,J= 7.5 Hz,3H,7-CH$_3$); 2.20 (s,3H,H-21); 5.83 (s broad, 1H,H-4); 6.05 (s,2H,H-17$^1$ and H-17$^2$).

Example 4

14,17-Etheno-19-norpregna-4,9-diene-3,20-dione a) 14,17-Etheno-19-norpregn-5(10)-ene-3,20-dione A solution of 2.1 g of oxalic acid dihydrate in 30 ml of water is instilled in a suspension of 3.0 g of the compound, described under 1d), in 60 ml of acetone with stirring at room temperature. After 2 hours, it is mixed with 150 ml of concentrated sodium bicarbonate solution and extracted three times with ethyl acetate. The combined organic phases are washed with concentrated sodium chloride solution, dried on sodium sulfate, filtered out and concentrated by evaporation. The residue is chromatographed on silica gel with a mixture of ethyl acetate and hexane. 1.51 g of 4a) is obtained.

Flash point: 96–110° C. $[\alpha]_D^{20}$=+231.6° (CHCl$_3$; c=0.505).

$^1$H-NMR (CDCl$_3$): δ=1.03 ppm (s,3H,H-18); 2.20 (s,3H, H-21); 2.72 and 2.82 (2d broad, J=20 Hz, 1H,H-4 each); 6.04 and 6.10 (2d,J=6 Hz, 1H,H-17$^1$ and H-17$^2$ each).

b) 14,17-Etheno-19-norpregna-4,9-diene-3,20-dione

A solution of 500 mg of the compound, described under 4a), in 6.5 ml of pyridine is mixed with stirring with 530 mg of pyridinium bromide perbromide for one hour at room temperature and then for another 2 hours at 50° C. After cooling, the reaction mixture is stirred into 20 ml of 6N hydrochloric acid and extracted three times with ethyl acetate. The combined organic phases are washed with water and concentrated sodium chloride solution, dried on sodium sulfate, filtered out and concentrated by evaporation. The residue is chromatographed on silica gel with a mixture of ethyl acetate and hexane. 0.31 g of 4b) is obtained.

Flash point: 152–158° C. $[\alpha]_D^{20}$=−200° (CHCl$_3$, c=0.496).

$^1$H-NMR (CDCl$_3$): d=1.04 ppm (s,3H,H-18); 2.20 (s,3H, H-21); 5.72 (s broad,3H,H-4); 6.03 (s,2H,H-17$^1$ and H-17$^2$).

Example 5

21-Hydroxy-14,17-etheno-19-norpregn-4-ene-3,20-dione a) 3,3;20,20-Bis[2,2-dimethyl-1,3-propanediylbis(oxy)]-14,17-etheno-19-norpregn-5(10)-ene 2.08 g of 2,2-dimethylpropane-1,3-diol, 2.7 ml of trimethyl orthoformate and 190 mg of p-toluenesulfonic acid are added to a solution of 3.2 g of the compound, described under 1e), in 30 ml of toluene with stirring. After 2 hours, it is mixed with 5 ml of triethylamine, diluted with ethyl acetate, washed five times with water and once with concentrated sodium chloride solution, dried on sodium sulfate, filtered out and concentrated by evaporation. The residue is chromatographed on silica gel with a mixture of ethyl acetate and hexane. 3.85 g of 5a) is obtained as foam.

$^1$H-NMR (CDCl$_3$): d=0.72, 0.88, 0.94, 1.07 and 1.19 ppm (5s,15H,ketal-CH$_3$ and H-18); 1.43 (s,3H,H-21); 3.17–3.78 (m,8H,ketal-OCH$_2$); 5.88 and 5.95 (2d,J=6 Hz, 1H,H-17$^1$ and H-17$^2$ each).

b) 3,3-[2,2-Dimethyl-1,3-propanediylbis(oxy)]-14,17-etheno-19-norpregn-5(10)-en-20-one A solution of 3.85 g of the compound, described under 5a), in 50 ml of dichloromethane is mixed with 11 g of silica gel (0.063–0.2 mm) and 1.1 ml of concentrated aqueous oxalic acid solution and stirred intensively for 30 minutes. 100 ml of 1N sodium hydroxide solution and 100 ml of dichloromethane are added, stirred for five minutes, allowed to settle, filtered, the residue is washed with dichloromethane, the combined organic phases are washed with concentrated sodium chloride solution, dried on sodium sulfate, filtered and concentrated by evaporation. The residue is chromatographed on silica gel with a mixture of ethyl acetate and hexane. 1.93 g of 5b) is obtained as foam.

$^1$H-NMR (CDCl$_3$): d=0.85 and 0.88 ppm (2s,6H,ketal-CH$_3$); 1.08 (s,3H,H-18); 2.18 (s,3H,H-21); 3.42–3.70 (m,4H, ketal-OCH$_2$); 5.98 and 6.07 (2d,J=6 Hz, 1H,H-17$^1$ and H-17$^2$ each).

c) 3,3-[2,2-Dimethyl-1,3-propanediylbis(oxy)]-21-iod-14,17-etheno-19-norpregn-5(10)-en-20-one 3.9 ml of a 1.6 molar solution of n-butyllithium in hexane is instilled in a solution of 1.9 ml of N-cyclo-hexyl isopropylamine in 10 ml of tetrahydrofuran at −40° C. After 15 minutes of stirring, a solution of 1.93 g of the substance, described under 5b), in 15 ml of tetrahydrofuran is instilled. After 30 minutes of stirring at −30° C., the solution is cooled to −50° C., and then pumped via a teflon hose to a solution of 1.37 g of iodine in 10 ml of tetrahydrofuran that is cooled to −50° C. The reaction mixture is heated to room temperature within 2 hours, then poured on concentrated ammonium chloride solution and extracted with ethyl acetate. The organic phase is washed with concentrated sodium thiosulfate solution and concentrated sodium bicarbonate solution, dried on sodium sulfate and concentrated by evaporation. 2.6 g of 5c) is obtained as light yellow resin, which is reacted in the next step without further purification.

$^1$H-NMR (CDCl$_3$): d=0.88 ppm (s,6H,ketal-CH$_3$); 1.08 (s,3H,H-18); 3.42–3.70 (m,4H,ketal-OCH$_2$); 3.90 and 3.99 (2d,J=12 Hz, 1H,H-21 each); 6.07–6.18 (m,2H,H-17$^1$ and H-17$^2$).

d) 21-(Acetyloxy)-3,3-[2,2-dimethyl-1,3-propanediylbis-(oxy)]-14,17-etheno-19-norpregn-5(10)-en-20-one A solution of 2.6 g of the substance, described under 5c), in 10 ml of dimethylformamide is mixed with 4.9 g of potassium acetate, stirred for 80 minutes at 80° C., poured on water after cooling and extracted with ethyl acetate. The organic phase is washed with concentrated sodium chloride solution, dried on sodium sulfate and concentrated by evaporation. 1.99 g of 5d) is obtained as colorless resin, which is reacted in the next step without further purification.

$^1$H-NMR (CDCl$_3$): d=0.88 ppm (s,6H,ketal-CH$_3$); 1.08 (s,3H,H-18); 2.17 (s,3H,acetyloxy-CH$_3$); 3.42–3.72 (m,4H, ketal-OCH$_2$); 4.67 and 4.85 (2d,J=15 Hz, 1H,H-21 each); 5.99 and 6.12 (2d,J=6 Hz, 1H,H-17$^1$ and H-17$^2$ each).

e) 21-(Acetyloxy)-14,17-etheno-19-norpregn-5-(10)-ene-3,20-dione

A solution of 1.99 g of the substance, described under 5d), in 10 ml of tetrahydrofuran is mixed with 100 ml of 70% acetic acid and stirred for 60 minutes at room temperature and then for 60 minutes at 40° C. The reaction mixture is poured on water, neutralized with sodium hydroxide solution and extracted three times with ethyl acetate. The combined organic phases are washed with concentrated sodium chloride solution, dried on sodium sulfate and concentrated by evaporation. The residue is chromatographed on silica gel with a mixture of ethyl acetate and hexane. 1.15 g of 5e) is obtained.

Flash point: 126–128° C. $[\alpha]_D^{20}$=+199.6° (CHCl$_3$, c=0.500).

$^1$H-NMR (CDCl$_3$): d=0.90 ppm (s,3H,H-18); 2.18 (s,3H, acetyloxy-CH$_3$); 4.67 and 4.84 (2d,J=16 Hz, 1H,H-21 each); 6.02 and 6.14 (2d,J=6 Hz, 1H,H-17$^1$ and H-17$^2$ each).

f) 21-(Acetyloxy)-14,17-etheno-19-norpregn-4-ene-3,20-dione

A solution of 500 mg of the substance, described under 5e), in 25 ml of acetone is mixed with 1 ml of 4N hydrochloric acid, stirred for 30 minutes at room temperature and then evaporated to dryness. 500 mg of 5f) is obtained as foam, which is reacted in the next step without further purification.

$^1$H-NMR (CDCl$_3$): d=0.93 ppm (s,3H,H-18); 2.18 (s,3H, acetyloxy-CH$_3$); 4.68 and 4.83 (2d,J=16 Hz, 1H,H-21 each); 5.86 (s broad,1H,H-4); 6.02 and 6.10 (2d,J=6 Hz, 1H,H-17$^1$ and H-17$^2$ each).

g) 21-Hydroxy-14,17-etheno-19-norpregn-4-ene-3,20-dione

A solution of 500 mg of the substance, described under 5f), in 15 ml of methanol is mixed with 1.8 ml of 10% aqueous potassium carbonate solution, stirred for 30 minutes at room temperature and then poured on water. It is acidified with 1N hydrochloric acid to pH 5, extracted three times with ethyl acetate, the combined organic phases are washed with concentrated sodium chloride solution, dried on sodium sulfate, filtered and concentrated by evaporation. The residue is chromatographed on silica gel with a mixture of ethyl acetate and hexane. 282 mg of 5g) is obtained.

Flash point: 160–163° C. $[\alpha]_D^{20}$=+162.3° (CHCl$_3$, c=0.510).

$^1$H-NMR (CDCl$_3$): d=0.95 ppm (s,3H,H-18); 3.32 (t, J=5 Hz,1H,OH); 4.23 and 4.42 (2dd,J=16 Hz and 5 Hz, 1H,H-21 each); (5.87 (s broad,1H,H-4); 5.87 and 6.10 (2d,J=6 Hz, 1H,H-17$^1$ and H-17$^2$ each).

Example 6

21-Hydroxy-14,17-etheno-19-norpregna-4,9-diene-3,20-dione a) 21-(Acetyloxy)-14,17-etheno-19-norpregna-4,9-diene-3,20-dione 540 mg of the substance described under 5c) is reacted according to the method described in Example 4b). 292 mg of 6a) is obtained.

Flash point: 182–184° C. $[\alpha]_D^{20}$=−106.6° (CHCl$_3$, c=0.495).

$^1$H-NMR (CDCl$_3$): d=1.04 ppm (s,3H,H-18); 2.19 (s,3H, acetyloxy-CH$_3$); 4.69 and 4.83 (2d,J=16 Hz, 1H,H-21 each); 5.72 (s broad,1H,H-4); 6.02 and 6.10 (2d,J=6 Hz, 1H,H-17$^1$ and H-17$^2$ each).

b) 21-Hydroxy-14,17-etheno-19-norpregna-4,9-diene-3,20-dione 270 mg of the substance described under 6a) is reacted according to the method described in Example 5g). 159 mg of 6b) is obtained.

Flash point: 143–146° C. $[\alpha]_D^{20}$=−171.4° (CHCl$_3$, c=0.505).

$^1$H-NMR (CDCl$_3$): d=1.04 ppm (s,3H,H-18); 3.33 (s broad,1,OH); 4.24 and 4.43 (2d broad,J=16 Hz, 1H,H-21 each); 5.72 (s broad,1H,H-4); 5.95 and 6.10 (2d,J=6 Hz, 1H,H-17$^1$ and H-17$^2$ each).

Example 7

21-Methyl-14,17-etheno-19-norpregn-4-ene-3,20-dione a) 3-Methoxy-21-methyl-14,17-etheno-19-norpregna-1,3,5 (10)-trien-20-one 6.6 ml of a 1.6 molar solution of n-butyllithium in hexane is instilled in a solution of 1.5 ml of diisopropylamine in 15 ml of tetrahydrofuran at −20° C., then stirred for 30 more minutes at 0° C., then a solution of 2.4 g of the substance described under 1b) and 0.78 ml of 1,3-dimethylimidazolin-2-one in 46 ml of tetrahydrofuran are instilled at −30° C. and allowed to stir for 30 more minutes at −30° C. Then, 0.66 ml of methyl iodide is instilled and allowed to heat to 0° C. The reaction mixture is stirred into concentrated ammonium chloride solution, diluted with water, extracted three times with ethyl acetate, the combined organic phases are washed with concentrated sodium chloride solution, dried on sodium sulfate, filtered and concentrated by evaporation. The residue is crystallized from diisopropyl ether. 2.12 g of 7a) is obtained.

Flash point: 94° C. $[\alpha]_D^{20}$ =+170.8° (CHCl$_3$, c=0.505).

$^1$H-NMR (CDCl$_3$): d=0.89 ppm (s,3H,H-18); 1.08 (t, J=7.5 Hz,3H,H-22); 3.79 (s,3H,3-OCH$_3$); 6.05 and 6.12 (2d, J=6 Hz, 1H,H-17$^1$ and H-17$^2$ each); 6.64 (d,J=3 Hz,1H,H-4); 6.72 (dd,J=9, 3 Hz,1H,H-2); 7.22 (d,J=9 Hz,1H,H-1).

b) 21-Methyl-14,17-etheno-19-norpregn-4-en-20-ol-3-one 1.9 g of the substance described under 7a) is reacted according to the method described in Example 1d). The crude product is chromatographed on silica gel with a mixture of ethyl acetate and hexane. 750 mg of intermediate product is obtained, which is reacted according to the method described in Example 1e). After chromatography on silica gel with a mixture of ethyl acetate and hexane, 317 mg of 7b) is obtained.

$^1$H-NMR (CDCl$_3$): d=0.89 (0.92) ppm (s,3H,H-18); 1.05 (1.03) (t,J=7.5 Hz,3H,H-22); 3.70 (dd,J=8 and 3 Hz,1H,H-20); 5.83 (5.85) (s broad,1H,H-4); 5.89 and 5.94 (5.96 and 6.02) (2d,J=6 Hz, 1H,H-17$^1$ and H-17$^2$ each).

(Signals from the 2nd diastereomer in parentheses).

c) 21-Methyl-14,17-etheno-19-norpregn-4-ene-3,20-dione

A solution of 300 mg of the compound, described under 7b), in 40 ml of dichloromethane is added to a suspension of 1.67 g of pyridinium dichromate in 15 ml of dimethylformamide with stirring. The mixture is stirred for one hour at room temperature, then mixed with 50 ml of ethyl acetate, stirred for another hour and then filtered. The filtrate is washed five times with water and then with concentrated sodium chloride solution, dried on sodium sulfate, filtered out and concentrated by evaporation. The residue is purified by means of HPLC. 100 mg of 7c) is obtained.

Flash point: 140–149° C. $[\alpha]_D^{20}$=+147.0° (CHCl$_3$; c=0.510).

$^1$H-NMR (CDCl$_3$): d=0.90 ppm (s,3H,H-18); 1.06 (t, J=7.5 Hz,3H,H-22); 5.86 (s broad,1H,H-4); 6.02 (s,2H,H-17$^1$ and H-17$^2$).

Example 8

21-Methyl-14,17-etheno-19-norpregna-4,9-diene-3, 20-dione a) 20,20-[1,2-Ethanediylbis(oxy)]-3-methoxy-31-methyl-14,17-etheno-19-norpregna-1,3,5(10)-triene 62 ml of ethylene glycol, 52 ml of trimethyl orthoformate and 1.0 g of p-toluenesulfonic acid are added to a solution of 21.3 g of the compound, described under 7a), in 250 ml of toluene at room temperature. It is heated to 60° C. for 8 hours. After cooling, 15 ml of triethylamine and 250 ml of ethyl acetate are added, and the mixture is washed three times with concentrated sodium bicarbonate solution. The organic phase is dried on potassium carbonate, filtered out and concentrated by evaporation. 27 g of 8a) is obtained, which is reacted in the next step without further purification.

$^1$H-NMR (CDCl$_3$): d=0.94 ppm (t,J=7.5 Hz,3H,H-22); 0.96 (s,3H,H-18); 3.78 (s,3H,3-OCH$_3$); 3.95–4.18 (m,4H, 20-OCH$_2$CH$_2$O—); 5.98 (s,2H,H-17$^1$ and H-17$^2$); 6.64 (d,J=3 Hz, 1H,H-4); 6.72 (dd,J=9, 3 Hz,1H,H-2); 7.21 (d,J=9 Hz,1H,H-1).

b) 20,20-[1,2-Ethanediylbis(oxy)]-3-methoxy-21-methyl-14,17-etheno-19-norpregna-2,5(10)-diene 27 g of the substance, described under 8a), is reacted according to the method described in Example 1d). 18.9 g of 8b) is obtained.

$^1$H-NMR (CDCl$_3$): d=0.93 ppm (t,J=7.5 Hz,3H,H-22); 0.95 (s,3H,H-18); 3.56 (s,3H,3-OCH$_3$); 3.93–4.10 (m,4H, 20-OCH$_2$CH$_2$O—); 4.62–4.67 (m,1H,H-2); 5.92 (s,2H,H-17$^1$ and H-17$^2$).

c) 20,20-[1,2-Ethanediylbis(oxy)]-21-methyl-14,17-etheno-19-norpregn-5(10)-en-3-one A solution of 18.2 g of the substance, described under 8b), in 700 ml of tetrahydrofuran is mixed with stirring with 250 ml of concentrated ammonium chloride solution and 18 ml of concentrated oxalic acid solution and stirred for 6 hours. Then, it is diluted with water and extracted three times with ethyl acetate. The combined organic phases are washed with concentrated sodium chloride solution, dried on sodium sulfate, filtered out and concentrated by evaporation. The residue is chromatographed on silica gel with a mixture of ethyl acetate and hexane. 11.0 g of 8c) is obtained as foam.

$[\alpha]_D^{20}$=+169.6° (CHCl$_3$; c=0.510).

$^1$H-NMR (CDCl$_3$): δ=0.92 ppm (5,J=7.5 Hz,3H,H-22); 0.97 (s,3H,H-18); 2.72 and 2.82 (2d broad,J=20 Hz, 1H,H-4 each); 3.95–4.12 (m,4H,20-OCH$_2$CH$_2$O—); 5.87–5.98 (m,2H,H-17$^1$ and H-17$^2$).

d) 21-Methyl-14,17-etheno-19-norpregna-4,9-diene-3,20-dione 11 g of the substance described under 8c) is reacted according to the method described in Example 4b). 3.75 g of 8d) is obtained.

Flash point: 145–146° C. $[\alpha]_D^{20}$=180.1° (CHCl$_3$, c=0.510).

$^1$H-NMR (CDCl$_3$): d=1.03 ppm (s,3H,H-18); 1.08 (t, J=7.5 Hz,3H,H-22); 5.72 (s broad,3H,H-4); 6.03 (s,2H,H-17$^1$ and H-17$^2$).

Example 9

21-Methyl-14,17-etheno-19-norpregna-4,9,11-triene-3,20-dione a) 3,3-[2,2-Dimethyl-1,3-propanediylbis(oxy)]-21-methyl-14,17-etheno-19-norpregna-5(10),9(11)-dien-20-one 2.87 g of 2,2-dimethylpropane-1,3-diol, 1.4 ml of trimethyl orthoformate and 100 mg of p-toluenesulfonic acid are added to a solution of 3.5 g of the compound, described under 8d), in 30 ml of dichloromethane with stirring. After 3 hours, it is diluted with dichloromethane, washed with water and with concentrated sodium chloride solution, dried on sodium sulfate, filtered out and concentrated by evaporation. The residue is chromatographed on silica gel with a mixture of ethyl acetate and hexane. 3.84 g of 9a) is obtained as foam.

$^1$H-NMR (CDCl$_3$): d=0.82 and 0.89 ppm (2s,6H,ketal-CH$_3$); 1.09 (s,3H,H-18); 1.09 (t,J=7.5 Hz,3H,H-22); 3.42–3.52 (m,2H,ketal-OCH$_2$); 3.57–3.68 (m,2H,ketal-OCH$_2$); 5.45–5.53 (m,1H,H-11); 6.03 and 6.12 (2d,J=6 Hz, 1H,H-17$^1$ and H-17$^2$ each).

b) 21-Methyl-14,17-etheno-19-norpregna-5(10),9(11)-diene-3,20-dione 500 mg of the compound described under 9a) is dissolved by ultrasound in 25 ml of 70% acetic acid and 5 ml of tetrahydrofuran and then stirred at room temperature for 4 hours. Then, it is neutralized with stirring with concentrated sodium bicarbonate solution. It is extracted three times with ethyl acetate, the combined organic phases are washed with concentrated sodium chloride solution, dried on sodium sulfate, filtered out and concentrated by evaporation. 480 mg of 9b) is obtained, which is reacted in the next step without further purification.

$^1$H-NMR (CDCl$_3$): δ=0.87 ppm (s,3H,H-18); 1.08 (t, J=7.5 Hz,3H,H-22); 2.91 (s broad,2H,H-4); 5.53–5.60 (m,1H, H-11); 6.07 and 6.13 (2d,J=6 Hz, 1H,H-17$^1$ and H-17$^2$ each).

c) 21-Methyl-14,17-etheno-19-norpregna-4,9,11-triene-3, 20-dione 480 mg of the compound described under 9b) is dissolved in 40 ml of dichloromethane and mixed with 600 mg of 2,3-dichloro-5,6-dicyano-p-benzoquinone. It is stirred for 4 hours at room temperature, filtered, the filtrate is washed with concentrated sodium bicarbonate solution, concentrated sodium thiosulfate solution and again with concentrated sodium bicarbonate solution, dried on sodium sulfate, filtered out and concentrated by evaporation. The residue is chromatographed on silica gel with a mixture of ethyl acetate and cyclohexane. 206 mg of 9c) is obtained.

Flash point: 117–119° C. $[\alpha]_D^{20}$=−278.8° (CHCl$_3$, c=0.500).

$^1$H-NMR (CDCl$_3$): d=0.97 ppm (s,3H,H-18); 1.11 (t, J=7.5 Hz,3H,H-22); 5.80 (s broad,3H,H-4); 5.99 and 6.08 (2d, J=6 Hz, 1H,H-17$^1$ and H-17$^2$ each); 6.04 (d,J=12 Hz; 1H,H-11); 6.44 (d,J=12 Hz;1H,H-12).

Example 10

17$^1$-Methyl-14,17-etheno-19-norpregn-4-ene-3,20-dione a) 3-Methoxy-16-methyl-19-norpregna-1,3,5(10),14,16-pentaen-20-one A suspension of 15.2 g of copper(I) iodide in 50 ml of diethyl ether is mixed at 0° C. drop by drop with 90 ml of a 1.6 molar solution of methyllithium in diethyl ether. After 30 minutes of stirring, 12 ml of triethylamine and then 11 ml of trimethylchlorosilane are added at −70° C. drop by drop. Then, a solution of 15 g of the compound, described under 1a), in 220 ml of tetrahydrofuran is instilled. It is allowed to stir for 2 more hours at −70° C., then 100 ml of concentrated ammonium chloride solution is added, it is allowed to heat to room temperature, shaken with 400 ml of ethyl acetate, solid components are filtered out and the aqueous phase is extracted again with ethyl acetate. The combined organic phases are washed four times with semiconcentrated ammonium chloride solution, dried on sodium sulfate, filtered out and concentrated by evaporation. The residue is dissolved by ultrasound in 500 ml of acetonitrile. 10.9 g of palladium(II) acetate is added to the solution and heated to 80° C. for 20 hours. After cooling, 400 ml of ethyl acetate is added, suctioned off on Celite and concentrated by evaporation. The residue is chromatographed on silica gel with a mixture of ethyl acetate and n-hexane. 5.03 g of 10a) is obtained.

Flash point: 166–167° C. $[\alpha]_D^{20}$ =+459.2° (CHCl$_3$, c=0.505).

$^1$H-NMR (CDCl$_3$): δ=1.22 ppm (s,3H,H-18); 2.37 and 2.40 (2s,6H,16-CH$_3$ and H-21); 3.80 (s,3H,3-OCH$_3$); 5.92 (d,J=2 Hz,1H,H-15); 6.68 (d,J=3 Hz,1H,H-4); 6.75 (dd,J=9, 3 Hz,1H,H-2); 7.25 (d,J=9 Hz,1H,H-1).

b) 3-Methoxy-17$^1$-methyl-14,17-etheno-19-norpregna-1,3,5 (10)trien-20-one 5.0 g of the compound described under 10a) is reacted according to the method described in Example 1b). 3.38 g of 10b) is obtained as foam.

$^1$H-NMR (CDCl$_3$): d=0.85 ppm (s,3H,H-18); 1.74 (s broad,17$^1$-CH$_3$); 2.20 (s,3H,H-21); 3.79 (s,3H,3-OCH$_3$); 5.67 (s broad,H-17$^2$); 6.66 (d,J=3 Hz,1H,H-4); 6.73 (dd,J=9,3 Hz, 1H,H-2); 7.22 (d,J=9 Hz,1H,H-1).

c) 17$^1$-Methyl-14,17-etheno-19-norpregn-4-ene-3,20-dione 500 mg of the compound described under 10b) is reacted according to the methods described in Examples 1c), 1d) and 1e). 344 mg of 10c) is obtained.

Flash point: 137° C. $[\alpha]_D^{20}$=+109.6° (CHCl$_3$, c=0.500).

$^1$-H-NMR (CDCl$_3$): d=0.86 ppm (s,3H,H-18); 1.70 (s broad,17$^1$-CH$_3$); 2.16 (s,3H,H-21); 5.58 (s broad,1H,H-17$^2$); 5.84 (s broad,1H,H-4).

Example 11

17$^1$-Methyl-14,17-etheno-19-norpregna-4,6-diene-3,20-dione 250 mg of the compound described under 10c) is reacted according to the methods described in Examples 2a) and 2b). 102 mg of 11) is obtained.

Flash point: 132–136° C.

$^1$H-NMR (CDCl$_3$): d=0.89 ppm (s,3H,H-18); 1.69 (s broad, 17$^1$-CH$_3$); 2.17 (s,3H,H-21); 5.47 (s broad,1H,H-17$^2$); 5.80 (s broad,1H,H-4); 6.17–6.30 (m,2H,H-6 and H-7).

Example 12

(17$^1$R)-17$^1$-Methyl-14,17-ethano-19-norpregn-4-ene-3,20-dione a) 3-Methoxy-17$^1$-methyl-14,17-ethano-19-norpregna-1,3,5 (10)-trien-20-one 2.75 g of the compound described under 10b) is dissolved in a shaking apparatus in 125 ml of tetrahydrofuran. 765 mg of palladium on activated carbon (10%) is added, the apparatus is placed under hydrogen and shaken until the hydrogen absorption has ended. After filtration of the solution on Celite, it is concentrated by evaporation in a vacuum. 2.9 g of 12a) is obtained as foam.

$^1$H-NMR (CDCl$_3$): d=0.88 (0.92) ppm (s,3H,H-18); 0.99 (1.10) (d,J=7.5 Hz,3H,17$^1$-CH$_3$); 2.08 (2.11) (s,3H,H-21); 3.78 (s,3H,3-OCH$_3$); 6.62 (d,J=3 Hz,1H,H-4); 6.73 (dd,J=9, 3 Hz,1H,H-2); 7.22 (d,J=9 Hz,1H,H-1).

(Signals from the 2nd diastereomer in parentheses)

b) (17$^1$R)-17$^1$-Methyl-14,17-ethano-19-norpregn-5(10)-ene-3,20-dione 2.9 g of the compound described under 12a) is reacted according to the methods described in Examples 1c), 1d) and 8c). 209 mg of 12b), 310 mg of the two C-17$^1$ epimers of 20,20-[1,2-ethanediylbis(oxy)]-17$^1$-methyl-14,17-ethano-19-norpregn-4-en-3-one in a mixture with (17'S)-17'-methyl-14,17-ethano-19-norpregn-5(10)-ene-3,20-dione as well as 1.36 g of the two C-17$^1$ epimers of 20,20-[1,2-ethanediylbis(oxy)]-17$^1$-methyl-14,17-ethano-19-norpregn-5(10)-en-3-one are obtained.

$^1$H-NMR (CDCl$_3$): d=0.90 ppm (s,3H,H-18); 1.07 (d,J= 7.5 Hz,3H,17$^1$-CH$_3$); 2.06 (s,3H,H-21).

c) (17$^1$R)-17$^1$-Methyl-14,17-ethano-19-norpregn-4-ene-3,20-dione 190 mg of 12b) is reacted according to the method described in Example 1e). 105 mg of 12c) is obtained.

$^1$H-NMR (CDCl$_3$): d=0.95 ppm (s,3H,H-18); 1.05 (d, J=7.5 Hz,3H,17$^1$-CH$_3$); 2.07 (s,3H,H-21); 5.81 (s broad,1H, H-4).

Example 13

(17$^1$S)-17$^1$-Methyl-14,17-ethano-19-norpregn-4-ene-3,20-dione 300 mg of the mixture, described under 12b), of the two C-17$^1$ epimers of 20,20-[1,2-ethanediylbis(oxy)]-17$^1$methyl-14,17-ethano-19-norpregn-4-en-3-one and (17$^1$S)-17$^1$-methyl-14,17-ethano-19-norpregn-5(10)-ene-3, 20-dione, is reacted according to the method described in Example 1e). 77 mg of 12c) and 122 mg of 13) are obtained.

$^1$H-NMR (CDCl$_3$): d=0.68 ppm (dd,J=6 Hz and 13 Hz,1H, H-17$^2$); 0.92 (s,3H,H-18); 0.96 (d,J=7.5 Hz,3H,17$^1$-CH$_3$); 2.08 (s,3H,H-21); 5.82 (s broad,1H,H-4).

Examples 14 and 15

14: (17$^1$R)-17$^1$-Methyl-14,17-ethano-19-norpregna-4,9-diene-3,20-dione

15: (17$^1$S)-17$^1$-Methyl-14,17-ethano-19-norpregna-4,9-diene-3,20-dione 1.30 g of the mixture, described under 12b), of the two C-17$^1$ epimers of 20,20-[1,2-ethanediylbis(oxy)]-17$^1$-methyl-14,17-ethano-19-norpregn-5(10)-en-3-one is reacted according to the methods described in Examples 4b) and 1e). 200 mg of 14) and 120 mg of 15) are obtained. 14):

$^1$H-NMR (CDCl$_3$): d=1.04 ppm (s,3H,H-18); 1.06 (d, J=7.5 Hz,3H,17$^1$-CH$_3$); 2.07 (s,3H,H-21); 5.65 (s broad,1H, H-4). 15):

$^1$H-NMR (CDCl$_3$): d=0.76 ppm (dd,J=5 Hz and 12 Hz,1H, H-17$^2$); 0.95 (d,J=7.5 Hz,3H,17$^1$-CH$_3$); 1.01 (s,3H, H-18); 2.09 (s,3H,H-21); 5.66 (s broad,1H,H-4).

Example 16

14,17-Ethano-19-norpregna-4,9-diene-3,20-dione a) 3-Methoxy-16α-phenylsulfonyl-14,17-etheno-19-norpregna-1,3,5(10)-trien-20-one A mixture of 14.7 g of the substance described under 1a) and 24.0 g of phenyl vinyl sulfone is heated to 155° C. in 100 ml of benzene for 10 days. After cooling, the reaction mixture is concentrated by evaporation, and the residue is chromatographed on silica gel first with dichloromethane and then with a mixture of ethyl acetate and hexane. 14.9 g of 16a) is obtained.

Flash point: 178–179° C.

$^1$H-NMR (CDCl$_3$): δ=0.84 ppm (s,3H,H-18); 2.30 (s,3H,H-21); 3.77 (s,3H,3-OCH$_3$); 4.58 (dd,J=8, 4 Hz,1H,H-16); 6.48 and 6.50 (2d,J=5 Hz, 1H,H-17$^1$ and H-17$^2$ each); 6.64 (d, J=3 Hz,1H,H-4); 6.72 (dd,J=9, 3 Hz,1H,H-2); 7.18 (d,J=9 Hz, 1H,H-1); 7.52–7.87 (m,5H,SO$_2$C$_6$H$_5$).

b) 3-Methoxy-14,17-ethano-19-norpregna-1,3,5(10)-trien-20-ol 120 g of water-moistened Raney nickel is washed several times with ethanol and ultimately suspended in 900 ml of ethanol. 6.95 g of the substance described under 16a) is added to this suspension and refluxed for 16 hours. After cooling, it is decanted from Raney nickel, rewashed several times with ethanol and concentrated by evaporation. The residue is chromatographed on silica gel with a mixture of ethyl acetate and cyclohexane. 1.40 g of 3-methoxy-14,17-ethano-19-norpregna-1,3,5(10)-trien-20-one with a flash point of 140–142° C. and 2.70 g of 16b) are obtained.

Flash point: 90–100° C.

$^1$H-NMR (CDCl$_3$): δ=0.88 and 0.92 ppm (2s,3H,H-18); 1.12 and 1.18 (2d,J=6 Hz,3H,H-21); 3.78 (s,3H,3-OCH$_3$); 3.95 (q,J=6 Hz,1H,H-20); 6.63 (d,J=3 Hz,1H,H-4); 6.72 (dd,J=9, 3 Hz,1H,H-2); 7.21 (d,J=9 Hz,1H,H-1).

c) 3-Methoxy-14,17-ethano-19-norpregna-2,5(10)-dien-20-ol 5.50 g of the compound described under 16b) is reacted according to the method described in Example 1d). 5.50 g of 16c) is obtained.

$^1$H-NMR (CDCl$_3$): δ=0.87 and 0.90 ppm (2s,3H,H-18); 1.10 and 1.16 (2d,J=6 Hz,3H,H-21); 3.55 (s,3H,3-OCH$_3$); 3.87–3.98 (m,1H,H-20); 4.65 (m,1H,H-2).

d) 14,17-Ethano-19-norpregn-5(10)-en-20-ol-3-one 1.70 g of the compound described under 16c) is reacted according to the method described in Example 4a). 0.80 g of 16d) is obtained.

Flash point: 103–117° C.

$^1$H-NMR (CDCl$_3$); δ=0.87 and 0.90 ppm (2s,3H,H-18); 1.11 and 1.16 (2d,J=6 Hz,3H,H-21); 2.69 and 2.78 (2d, J=20 Hz,1H,H-4 each); 3.85–3.98 (m,1H,H-20).

e) 14,17-Ethano-19-norpregna-4,9-dien-20-ol-3-one

A solution of 0.80 g of the compound, described under 16d), in 10 ml of pyridine is instilled in a solution of 0.16 ml of bromine in 10 ml of pyridine under ice cooling and with stirring. After 3 hours, the reaction mixture is poured into 2N hydrochloric acid and adjusted to a pH between 4 and 5. It is extracted with ethyl acetate. The organic phase is washed with water and concentrated sodium chloride solution, dried on sodium sulfate, filtered out and concentrated by evaporation. The residue is chromatographed on silica gel with a mixture of ethyl acetate and hexane. 0.22 g of 16e) is obtained.

$^1$H-NMR (CDCl$_3$): δ=1.01 and 1.07 ppm (2s,3H,H-18); 1.12 and 1.15 (2d,J=6 Hz,3H,H-21); 3.88–4.00 (m,1H,H-20); 5.67 (s broad,1H,H-4).

f) 14,17-Ethano-19-norpregna-4,9-diene-3,20-dione 360 mg of pyridinium chlorochromate is added to a solution of 220 mg of the compound, described under 16e), in 20 ml of dichloromethane. The mixture is stirred for 2 hours at room temperature and then filtered. The filtrate is concentrated by evaporation and chromatographed on silica gel with a mixture of ethyl acetate and hexane. 130 mg of 16f) is obtained as foam.

$[α]_D^{20}$=−255.3° (CHCl$_3$, c=0.600).

$^1$H-NMR (CDCl$_3$): d=1.04 ppm (s,3H,H-18); 2.12 (s,3H,H-21); 5.67 (s broad,3H,H-4).

Example 17

14,17-Ethano-19-norpregna-4,6-diene-3,20-dione a) 14,17-Ethano-19-norpregn-4-ene-3,20-dione 5.50 g of the compound described under 16c) is reacted according to the methods indicated in Examples 1e) and 16f). 2.80 g of 17a) is obtained.

Flash point: 140–145° C. $[α]_D^{20}$=+67.6° (CHCl$_3$; c=0.550).

$^1$H-NMR (CDCl$_3$): d=0.94 ppm (s,3H,H-18); 2.10 (s,3H,H-21); 5.83 (s broad,1H,H-4).

b) 14,17-Ethano-19-norpregna-4,6-diene-3,20-dione 326 mg of the compound described under 17a) is reacted according to the methods indicated in Examples 2a) and 2b). 160 mg of 17c) is obtained.

Flash point: 126–132° C. $[α]_D^{20}$=+31.8° (CHCl$_3$; c=0.575).

$^1$H-NMR (CDCl$_3$): d=0.96 ppm (s,3H,H-18); 2.11 (s,3H,H-21); 5.78 (s broad,1H,H-4); 6.14–6.23 (m,2H,H-6 and H-7).

Example 18

21-Methyl-14,17-ethano-19-norpregn-4-ene-3,20-dione a) 3-Methoxy-21-methyl-14,17-ethano-19-norpregna-1,3,5(10)-trien-20-one 133 g of the compound described under 1b) is dissolved in a shaking apparatus in 2 l of ethyl acetate. 13 g of palladium on activated carbon (10%) is added, the apparatus is placed under hydrogen and shaken until the hydrogen absorption has ended. After filtration of the solution on Celite, it is concentrated by evaporation. After crystallization from ethyl acetate, 129 g of 18a) is obtained.

Flash point: 146–147° C. $[α]_D^{20}$=+66.7° (CHCl$_3$; c=0.490).

$^1$H-NMR (CDCl$_3$): d=0.90 ppm (s,3H,H-18); 2.23 (s,3H,H-21); 3.78 (s,3H,3-OCH$_3$); 6.63 (d,J=3 Hz,1H,H-4); 6.73 (dd, J=9, 3 Hz,1H,H-2); 7.22 (d,J=9 Hz,1H,H-1).

b) 3-Methoxy-21-methyl-14,17-ethano-19-norpregna-1,3,5(10)-trien-20-one 5.00 g of the compound described under 18a) is reacted according to the method indicated in Example 7a). 4.4 g of 18b) is obtained as foam.

$[α]_D^{20}$=+71.3° (CHCl$_3$; c=0.545).

$^1$H-NMR (CDCl$_3$): d=0.89 ppm (s,3H,H-18); 1.03 (t, J=7 Hz,3H,H-22); 2.40–2.50 (m,2H,H-21); 3.78 (s,3H,3-OCH$_3$); 6.63 (d,J=3 Hz,1H,H-4); 6.72 (dd,J=9, 3 Hz,1H,H-2); 7.22 (d,J=9 Hz,1H,H-1).

c) 3-Methoxy-21-methyl-14,17-ethano-19-norpregna-2,5(10)-dien-20-ol 2.70 g of the compound described under 18b) is reacted according to the method indicated in Example 1d). 1.75 g of 18c) is obtained.

Flash point: 137–143° C.

$^1$H-NMR (CDCl$_3$): d=0.86 ppm (s,3H,H-18); 0.98 (t, J=7 Hz,3H,H-22); 3.55 (s,3H,3-OCH$_3$); 4.66 (s broad,1H,H-2).

d) 21-Methyl-14,17-ethano-19-norpregn-4-en-20-ol-3-one 356 mg of the compound described under 18c) is reacted according to the method indicated in Example 1e). 300 mg of 18d) is obtained.

$^1$H-NMR (CDCl$_3$): d=0.91 ppm (s,3H,H-18); 0.98 (t, J=7 Hz, 3H,H-22); 3.55–3.63 (m,1H,H-20); 5.81 (s broad,1H, H-4).

e) 21-Methyl-14,17-ethano-19-norpregn-4-ene-3,20-dione 300 mg of the compound described under 18d) is reacted according to the method indicated in Example 14f). 200 mg of 18e) is obtained.

Flash point: 123–128° C. $[\alpha]_D^{20}$=+63.8° (CHCl$_3$; c=0.525).

$^1$H-NMR (CDCl$_3$): d=0.93 ppm (s,3H,H-18); 1.00 (t, J=7 Hz,3H,H-22); 5.82 (s broad,1H,H-4).

Example 19

21-Methyl-14,17-ethano-19-norpregna-4,9-diene-3,20-dione 770 mg of the compound described under 18c) is reacted according to the methods indicated in Examples 4a), 4b) and 16f). 170 mg of 19) is obtained.

Flash point: 130° C. $[\alpha]_D^{20}$=−251.2° (CHCl$_3$; c=0.470).

$^1$H-NMR (CDCl$_3$): d=1.02 ppm (t,J=7 Hz,3H,H-22); 1.05 (s,3H,H-18); 5.68 (s broad,1H,H-4).

Example 20

21-Methyl-14,17-ethano-19-norpregna-4,6-diene-3,20-dione 370 mg of the compound described under 18d) is reacted according to the methods indicated in Examples 2a), 2b) and 16f). 120 mg of 20) is obtained.

Flash point: 155–158° C. $[\alpha]_D^{20}$=+20.0° (CHCl$_3$; c=0.490).

$^1$H-NMR (CDCl$_3$): d=0.96 ppm (s,3H,H-18); 1.02 (t, J=7 Hz,3H,H-22); 5.78 (s broad,1H,H-4); 6.15–6.23 (m,2H,H-6 and H-7).

Example 21

21,21-Dimethyl-14,17-ethano-19-norpregna-4,9-diene-3,20-dione a) 3,3-[2,2-Dimethyl-1,3-propanediylbis(oxy)]-21-methyl-14,17-ethano-19-norpregna-5(10),9(11)-dien-20-one 18.3 g of the compound described under 18c) is reacted according to the methods indicated in Examples 4a), 4b), 9a) and 7c). 1.0 g of 21a) is obtained.

$^1$H-NMR (CDCl$_3$): d=0.85 and 0.90 ppm (2s,6H,ketal-CH$_3$); 1.03 (t,J=7 Hz,3H,H-22); 1.09 (s,3H,H-18); 3.42–3.52 (m,2H,ketal-OCH$_2$); 3.57–3.68 (m,2H,ketal-OCH$_2$); 5.50–5.55 (m,1H,H-11).

b) 21,21-Dimethyl-14,17-ethano-19-norpregna-4,9-diene-3,20-dione 210 mg of the compound described under 21a) is reacted according to the methods indicated in Examples 7a) and 1e). 108 mg of 21b) is obtained.

$^1$H-NMR (CDCl$_3$): d=1.01 ppm (d,J=6 Hz,6H,H-22,H-22'); 1.05 (s,3H,H-18); 5.68 (s broad,1H,H-4).

Example 22

6-Methyl-14,17-ethano-19-norpregna-4,6-diene-3,20-dione a) 6-Methylene-14,17-ethano-19-norpregn-4-ene-3,20-dione 6.10 g of the compound described under 17a) is reacted according to the method described in Example 2a) to the corresponding dienol ether, which is taken up as crude product in 60 ml of dimethylformamide and is mixed at 0° C. with a solution of 5.2 ml of phosphorus oxychloride in 30 ml of dimethyformamide. After one hour, the reaction mixture is instilled in concentrated sodium bicarbonate solution and extracted with ethyl acetate. The organic phase is washed with water and concentrated sodium chloride solution, dried on sodium sulfate, filtered out and concentrated by evaporation. 5.27 g of the 6-formyl compound is obtained as crude product, which is dissolved in 14 ml of ethanol and 28 ml of dimethylformamide and is mixed in portions with 0.66 g of sodium borohydride. After one hour, 7.5 ml of 2N sulfuric acid is instilled. After 15 minutes, the reaction mixture is diluted with 120 ml of water, neutralized with concentrated sodium bicarbonate solution and extracted with ethyl acetate. The organic phase is washed with water and concentrated sodium chloride solution, dried on sodium sulfate, filtered out and concentrated by evaporation. 4.31 g of 22a) is obtained as crude product.

$^1$H-NMR (CDCl$_3$): d=0.93 ppm (s,3H,H-18); 2.12 (s,3H, H-21); 4.94 and 5.18 (2s broad, 1H,6-=CH$_2$ each), 6.11 (s broad,1H,H-4).

b) 6-Methyl-14,17-ethano-19-norpregna-4,6-diene-3,20-dione 1.05 g of palladium on carbon (5%) is refluxed in 50 ml of methanol for 30 minutes and then mixed with a solution of 2.15 g of the compound, described under 22a), in 90 ml of methanol and refluxed for 90 minutes. The catalyst is filtered out and after the concentration by evaporation, the residue is chromatographed on silica gel with a mixture of ethyl acetate and hexane. 88 mg of 22b) is obtained.

$^1$H-NMR (CDCl$_3$): d=0.95 ppm (s,3H,H-18); 1.83 (s broad,1H,6-CH$_3$); 2.12 (s,3H,H-21); 5.93 and 5.99 (2s broad, 2H,H-4 and H-7).

Example 23

6α-Methyl-14,17-ethano-19-norpregn-4-ene-3,20-dione

A solution of 2.15 g of the compound, described under 22a), in 30 ml of ethanol is mixed with 3 ml of cyclohexane and 0.25 g of palladium on carbon (10%) and refluxed for 75 minutes. The catalyst is filtered out and after the concentration by evaporation, the residue is chromatographed on silica gel with a mixture of ethyl acetate and hexane. 140 mg of 23) is obtained.

$^1$H-NMR (CDCl$_3$): d=0.95 pm (s,3H,H-18); 1.12 (d, J=7 Hz,3H,6-CH$_3$); 2.12 (s,3H,H-21); 5.86 (s broad,1H,H-4).

Example 24

21-Hydroxy-14,17-ethano-19-norpregn-4-ene-3,20-dione 4.9 g of the compound described under 17a) is reacted according to the methods indicated in Examples 9a), 5c), 5d), 1e) and 5g). 253 mg of 24) is obtained.

$[\alpha]_D^{20}$=+65.9° (CHCl$_3$; c=0.525).

$^1$H-NMR (CDCl$_3$): d=0.95 ppm (s,3H,H-18); 3.35 (t, J=5 Hz,1H,21-OH), 4.24 and 4.27 (2d,J=5 Hz, 1H,H-21 each); 5.72 (s broad,1H,H-4).

Example 25

21-Hydroxy-14,17-ethano-19-norpregna-4,9-diene-3,20-dione 805 mg of the compound described under 16f) is reacted according to the methods indicated in Examples 9a), 5c), 5d), 1e) and 5g). 110 mg of 25) is obtained.

$[\alpha]_D^{20}$=−232.8° (CHCl$_3$; c=0.500).

$^1$H-NMR (CDCl$_3$): d=1.04 ppm (s,3H,H-18); 3.32 (t, J=5 Hz,1H,21-OH); 4.23 and 4.27 (2d,J=5 Hz, 1H,H-21 each); 5.68 (s broad,1H,H-4).

Examples 26 and 27

26: (21R)-21-Hydroxy-21-methyl-14,17-ethano-19-norpregna-4,9-diene-3,20-dione

27: (21S)-21-Hydroxy-21-methyl-14,17-ethano-19-norpregna-4,9-diene-3,20-dione 2.00 g of the compound described under 21a) is reacted according to the methods indicated in Examples 5c), 5d), 1e) and 5g). 640 mg of the 21-epimer mixture is obtained, which is separated by chromatography on silica gel with a mixture of ethyl acetate and hexane in 210 mg of 26) and 230 mg of 27).

26: $[\alpha]_D^{20}$=−1.6° (CHCl$_3$; c=0.495).

$^1$H-NMR (CDCl$_3$): d=1.03 ppm (s,3H,H-18); 1.32 (d, J=6 Hz,3H,H-22); 3.60 (d,J=6 Hz,1H,21-OH); 4.37–4.46 (m,1H, H-21); 5.68 (s broad,1H,H-4).

27: $[\alpha]_D^{20}$=−1.0° (CHCl$_3$; c=0.475)

$^1$H-NMR (CDCl$_3$): d=1.07 ppm (s,3H,H-18); 1.29 (d, J=6 Hz,3H,H-22), 3.40 (d,J=7 Hz,1H,21-OH), 4.33–4.44 (m,1H, H-21); 5.68 (s broad,1H,H-4).

Example 28

16α-Methyl-14,17-ethano-19-norpregn-4-ene-3,20-dione a) 3-Methoxy-20-oxo-14,17-etheno-19-norpregna-1,3,5 (10)-triene-16α-carboxylic acid methyl ester 19.4 g of the compound described in Example 1a), 37 ml of freshly distilled methyl acrylate and 200 mg of hydroquinone are left in a closed tube for 7 days at 120° C. After cooling and distilling off all volatile components under reduced pressure, the residue is chromatographed on silica gel with a mixture of ethyl acetate and hexane. 21.0 g of 28a) is obtained.

Flash point: 145–146° C. $[\alpha]_D^{20}$=+216.4° (CHCl$_3$; c=0.505).

$^1$H-NMR (CDCl$_3$): d=0.96 ppm (s,3H,H-18); 2.29 (s,3H, H-21); 3.60 (s,3H,CO$_2$CH$_3$); 3.78 (s,3H,3-OCH$_3$); 3.84 (dd, J=9.5 and 4.5 Hz,H-16); 6.15 and 6.27 (2d,J=6 Hz, 1H,H-17$^1$ and H-17$^2$ each); 6.64 (d,J=3 Hz,1H,H-4); 6.72 (dd,J=9 and 3 Hz,1H,H-2); 7.19 (d,J=9 Hz,1H,H-1).

b) 20,20-[1,2-Ethanediylbis(oxy)]-3-methoxy-14,17-etheno-19-norpregna-1,3,5(10)-triene-16α-carboxylic acid methyl ester 20.8 g of the compound described under 28a) is reacted according to the method indicated in Example 1c). 17.0 g of 28b) is obtained.

Flash point: 128–130° C. $[\alpha]_D^{20}$=+141.2° (CHCl$_3$; c=0.505).

$^1$H-NMR (CDCl$_3$): d=1.03 ppm (s,3H,H-18); 1.32 (s,3H, H-21); 3.38 (dd,J=9.5 and 4.5 Hz,1H,H-16); 3.60 (s,3H, CO$_2$CH$_3$); 3.78 (s,3H,3-OCH$_3$); 3.82–4.18 (m,4H,20-OCH$_2$CH$_2$O—); 6.00 and 6.23 (2d,J=6 Hz, 1H,H-17$^1$ and H-17$^2$ each); 6.63 (d,J=3 Hz,1H,H-4); 6.71 (dd,J=9 and 3 Hz,1H,H-2); 7.20 (d, J=9 Hz,1H,H-1).

c) 20,20-[1,2-Ethanediylbis(oxy)]-3-methoxy-14,17-etheno-19-norpregna-1,3,5(10)-triene-16α-methanol A solution of 8.2 g of the compound, described under 28b), in 150 ml of tetrahydrofuran is instilled in a suspension of 2.84 g of lithium aluminum hydride in 100 ml of tetrahydrofuran that is cooled to 0° C. After 2 hours of stirring at room temperature, it is slowly mixed with 5 ml of water. After another 20 minutes, it is filtered out on Celite, rewashed with dichloromethane, dried on sodium sulfate and concentrated by evaporation. 7.1 g of 28c) is obtained. For analytical purposes, a sample of pentane is crystallized.

Flash point: 162–164° C. $[\alpha]_D^{20}$=+104.2° (CHCl$_3$; c=0.520).

$^1$H-NMR (CDCl$_3$): d=1.05 ppm (s,3H,H-18); 1.48 (s,3H, H-21); 3.18–3.44 (m,2H,16-CH$_2$OH); 3.77 (s,3H,3-OCH$_3$); 4.01–4.12 (m,4H,20-OCH$_2$CH$_2$O—); 5.95 and 6.04 (2d,J=6 Hz, 1H,H-17$^1$ and H-17$^2$ each); 6.62 (d,J=3 Hz,1H,H-4); 6.72 (dd,J=9 and 3 Hz,1H,H-2); 7.21 (d,J=9 Hz,1H,H-1).

d) 20,20-[1,2-Ethanediylbis(oxy)]-3-methoxy-14,17-ethano-19-norpregna-1,3,5(10)-triene-16α-methanol 7.8 g of the compound described under 28c) is reacted according to the method indicated in Example 16a). 7.4 g of 28d) is obtained.

Flash point: 190–193° C. $[\alpha]_D^{20}$=+5.5° (CHCl$_3$; c=0.505).

$^1$H-NMR (CDCl$_3$): d=1.05 ppm (s,3H,H-18); 1.43 (s,3H, H-21); 3.54 (m,1H,16-CH$_2$OH); 3.78 (s,3H,3-OCH$_3$); 3.69–4.10 (m,5H,20-OCH$_2$CH$_2$O— and 16-CH$_2$OH); 6.62 (d,J=3 Hz,1H,H-4); 6.70 (dd,J=9 and 3 Hz,1H,H-2); 7.21 (d,J=9 Hz,1H,H-1).

e) 16α-(Bromomethyl)-20,20-[1,2-ethanediylbis(oxy)]-3-methoxy-14,17-ethano-19-norpregna-1,3,5(10)-triene 6.8 g of the compound described under 28d), 7.2 g of tetrabromomethane and 5.7 g of triphenylphosphine are stirred in 250 ml of dichloromethane for 16 hours at room temperature. After concentration by evaporation, it is chromatographed on silica gel with a mixture of ethyl acetate and hexane. 2.2 g of 28e) is obtained.

Flash point: 176–177° C. $[\alpha]_D^{20}$=−21.7° (CHCl$_3$; c=0.505).

$^1$H-NMR (CDCl$_3$): d=1.02 ppm (s,3H,H-18); 1.30 (s,3H, H-21); 3.34 (dd,J=10 and 12 Hz,16-CH$_2$Br); 3.78 (s,3H, 3-OCH$_3$); 3.82–4.06 (m,5H,20-OCH$_2$CH$_2$O— and 16-CH$_2$Br); 6.63 (d,J=3 Hz,1H,H-4); 6.71 (dd,J=9 and 3 Hz,1H,H-2); 7.20 (d, J=9 Hz,1H,H-1).

f) 20,20-[1,2-Ethanediylbis(oxy)]-3-methoxy-16α-methyl-14,17-ethano-19-norpregna-2,5(10)-diene 1.78 g of the compound described under 28e) is reacted according to the method indicated in Example 1d). 1.1 g of 28f) is obtained.

Flash point: 174–178° C. $[\alpha]_D^{20}$=+41.4° (CHCl$_3$; c=0.50).

$^1$H-NMR (CDCl$_3$): d=0.99 ppm (s,3H,H-18); 1.06 (d, J=7 Hz,16-CH$_3$); 1.25 (s,3H,H-21); 3.56 (s,3H,3-OCH$_3$); 3.78–4.01 (m,4H,20-OCH$_2$CH$_2$O—); 4.64 (m,1H,H-2).

g) 16α-Methyl-14,17-ethano-19-norpregn-4-ene-3,20-dione 1.05 g of the compound described under 28f) is reacted according to the method indicated in Example 1e). 0.7 g of 28g) is obtained.

Flash point: 172–173° C. $[\alpha]_D^{20}$=+52.7° (CHCl$_3$; c=0.485).

$^1$H-NMR (CDCl$_3$): d=0.96 ppm (s,3H,H-18); 0.96 (d, J=7 Hz,16-CH$_3$); 2.09 (s,3H,H-21); 5.81 (t,J=1 Hz,H-4).

Example 29

16α-Ethyl-14,17-ethano-19-norpregn-4-ene-3,20-dione a) 20,20-[1,2-Ethanediylbis(oxy)]-3-methoxy-14,17-ethano-19-norpregna-1,3,5(10)-triene-16α-carbaldehyde 2.7 g of the compound described under 28d) is reacted according to the method indicated in Example 7c). 2.4 g of 29a) is obtained.

¹H-NMR (CDCl₃); d=1.02 ppm (s,3H,H-18); 1.34 (s,3H, H-21); 3.78 (s,3H,3-OCH₃); 3.82–4.16 (m,4H,20-OCH₂CH₂O—); 6.61 (d,J=3 Hz,1H,H-4); 6.72 (dd,J=9 and 3 Hz,1H,H-2); 7.20 (d,J=9 Hz,1H,H-1); 9.88 (d,J=2 Hz,CHO).

b) 20,20-[1,2-Ethanediylbis(oxy)]-16α-ethenyl-3-methoxy-14,17-ethano-19-norpregna-1,3,5(10)-triene 10.7 g of methyltriphenylphosphonium bromide is suspended in 70 ml of tetrahydrofuran and mixed at 0° C. drop by drop with a total of 18 ml of a 1.6 molar solution of n-butyllithium in hexane. After 20 minutes of stirring at 0° C. and 1 hour of stirring at room temperature, 2.6 g of the compound, described under 29a), in 40 ml of tetrahydrofuran is instilled. After 2 hours, solid components are filtered out and it is concentrated by evaporation. The residue is dispersed between water and ethyl acetate, the organic phase is washed with concentrated aqueous sodium chloride solution, dried on sodium sulfate, filtered and concentrated by evaporation. After chromatography on silica gel with a mixture of ethyl acetate and hexane, 1.6 g of 29b) is obtained.

$[α]_D^{20}$=+13.7° (CHCl₃; c=0.510).
¹H-NMR (CDCl₃): d=1.03 ppm (s,3H,H-18); 1.38 (s,3H, H-21); 3.78 (s,3H,3-OCH₃); 3.84–4.03 (m,4H,20-OCH₂CH₂O—); 4.96–5.08 (m,2H,vinyl-CH₂); 6.02–6.17 (m,1H,vinyl-CH); 6.62 (d,J=3 Hz,1H,H-4); 6.71 (dd,J=9 and 3 Hz,1H,H-2); 7.21 (d, J=9 Hz,1H,H-1).

c) 20,20-[1,2-Ethanediylbis(oxy)]-16α-ethyl-3-methoxy-14,17-ethano-19-norpregna-1,3,5(10)-triene 1.0 g of the compound described under 29b) is reacted according to the method indicated in Example 16a). 1.0 g of 29c) is obtained.
¹H-NMR (CDCl₃): d=0.91 ppm (t,J=7 Hz,3H,16-ethyl-CH₃); 1.00 (s,3H,H-18); 1.30 (s,3H,H-21); 3.77 (s,3H, 3-OCH₃); 3.70–4.02 (m,4H,20-OCH₂CH₂O—); 6.61 (d,J=3 Hz,1H, H-4); 6.71 (dd,J=9 and 3 Hz,1H,H-2); 7.21 (d,J=9 Hz,1H,H-1).

d) 20,20-[1,2-Ethanediylbis(oxy)]-16α-ethyl-3-methoxy-14,17-ethano-19-norpregna-2,5(10)-diene 1.0 g of the compound described under 29c) is reacted according to the method indicated in Example 1d). 1.07 g of 29d) is obtained, which is further reacted as crude product.
¹H-NMR (CDCl₃): d=3.54 ppm (s,3H,3-OCH₃); 3.75–4.01 (m,4H,20-OCH₂CH₂O—); 4.63 (m,1H,H-2).

e) 16α-Ethyl-14,17-ethano-19-norpregn-4-ene-3,20-dione 0.97 g of the compound described under 29d) is reacted according to the method indicated in Example 1e). After chromatography on silica gel with a mixture of ethyl acetate and hexane, 0.56 g of 29e) is obtained, which is crystallized from diisopropyl ether.

Flash point: 145–147° C. $[α]_D^{20}$=+42.9° (CHCl₃; c=0.515).
¹H-NMR (CDCl₃): δ=0.96 ppm (t,J=7 Hz,3H,16-ethyl-CH₃); 0.96 (s,3H,H-18); 2.10 (s,3H, H-21); 5.81 (t,J=1 Hz,1H,H-4).

Example 30

16α-Ethenyl-14,17-ethano-19-norpregn-4-ene-3,20-dione a) 20,20-[1,2-Ethanediylbis(oxy)]-16a-ethenyl-3-methoxy-14,17-ethano-19-norpregna-2,5(10)-diene 0.5 g of the compound described under 29b) is reacted according to the method described in Example 1d). 0.5 g of 30a) is obtained, which is further processed without purification.
¹H-NMR (CDCl₃): d=1.02 ppm (s,3H,H-18); 1.23 (s,3H, H-21); 3.56 (s,3H,3-OCH₃); 3.82–4.02 (m,4H,20-OCH₂CH₂O—); 4.64 (m,1H,H-2); 4.93–5.07 (m,2H,vinyl-CH₂); 6.08 (m,1H, vinyl-CH).

b) 16α-Ethenyl-14,17-ethano-19-norpregn-4-ene-3,20-dione 0.49 g of 30a) is reacted according to the method described in Example 1e). After chromatography on silica gel with a mixture of ethyl acetate and hexane, 0.27 g of 30b) is obtained.

Flash point: 171° C. $[α]_D^{20}$=+26.7° (CHCl₃; c=0.515).
¹H-NMR (CDCl₃): d=1.00 ppm (s,3H,H-18); 2.08 (s,3H, H-21); 5.03–5.13 (m,2H,vinyl-CH₂); 5.72–5.87 (m,2H, vinyl-CH and H-4).

Example 31

16-Methylene-14,17-ethano-19-norpregn-4-ene-3,20-dione a) 20,20-[1,2-Ethanediylbis(oxy)]-3-methoxy-16-methylene-14,17-ethano-19-norpregna-1,3,5(10)-triene 27.86 g of the compound described under 29a) is dissolved in 268 ml of tetrahydrofuran and mixed at 0° C. with 26.6 g of potassium hexamethyl disilazide. After 1 hour, 17.8 ml of nonaflyl (nonafluorobutane sulfonic acid) fluoride is instilled. After 3 hours of stirring at room temperature, it is dispersed between water and ethyl acetate, and the organic phase is washed with concentrated sodium bicarbonate solution and common salt solution. After drying the organic phase on sodium sulfate, it is filtered, concentrated by evaporation and the residue is taken up in 546 ml of dimethylformamide. After the addition of 111.5 ml of triethylamine, 2.0 g of bis-(triphenylphosphine)-palladium-(II)-chloride and 19.5 ml of formic acid, it is heated to 80° C. for 7 hours and then left overnight at room temperature. After dispersing between ethyl acetate and water, the organic phase is washed with concentrated common salt solution, dried on sodium sulfate, filtered and concentrated by evaporation. The residue is chromatographed on silica gel with a mixture of ethyl acetate and hexane. 5.33 g of 31a) is obtained.

$[α]_D^{20}$=+21.1° (CHCl₃; c=0.530).
¹H-NMR (CDCl₃): d=0.99 ppm (s,3H,H-18); 1.44 (s,3H, H-21); 3.78 (s,3H,3-OCH₃); 3.87–4.07 (m,4H,20-OCH₂CH₂O—); 4.90 ppm (s broad,1H,16-methylene); 5.15 (s broad,1H,16-methylene); 6.63 (d,J=3 Hz,1H,H-4); 6.72 (dd,J=9 and 3 Hz, 1H,H-2); 7.23 (d,J=9 Hz,1H,H-1).

b) 16-Methylene-14,17-ethano-19-norpregn-4-ene-3,20-dione 510 mg of the compound described under 31a) is reacted according to the methods described in Examples 1d) and 1e). 440 mg of 31b) is obtained, which are digested with diisopropyl ether.
¹H-NMR (CDCl₃) d=1.09 ppm (s,3H,H-18); 2.22 (s,3H, H-21); 4.83 (s broad,1H,16-methylene); 4.90 (s broad,1H, 16-methylene); 5.82 (s broad,1H,H-4).

Example 32

16-Methylene-14,17-ethano-19-norpregna-4,9-diene-3,20-dione a) 20,20-[1,2-Ethanediylbis(oxy)]-16-methylene-14,17-ethano-19-norpregn-5(10)-en-3-one 6.8 g of the compound described under 31a) is reacted according to the methods described in Examples 1d) and 8c). After chromatography on silica gel with a mixture of ethyl acetate and hexane, 4.9 g of 32a) is obtained. In addition, 600 mg of 20,20-[1,2-ethanediylbis(oxy)]-16-methylene-14, 17-ethano-19-norpregn-4-en-3-one is obtained.
¹H-NMR (CDCl₃) for compound 32a): d=0.98 ppm (s,3H, H-18); 1.41 (s,3H,H-21); 2.68 and 2.78 (2d broad,J=20 Hz, 1H,H-4 each); 3.84–4.05 (m,4H,20-OCH$_2$CH$_2$O—); 4.89 (s broad, 1H,16-methylene); 5.12 (s broad,1H,16-methylene).

$^1$H-NMR (CDCl$_3$) for 20,20-[1,2-ethanediylbis(oxy)]-16-methylene-14,17-ethano-19-norpregn-4-en-3-one; d=1.00 ppm (s,3H,H-18); 1.42 (s,3H,H-21); 3.84–4.04 (m,4H, 20-OCH$_2$CH$_2$O—); 4.88 (s broad,1H,16-methylene); 5.13 (s broad,1H,16-methylene); 5.82 (s broad,1H,H-4).

b) 16-Methylene-14,17-ethano-19-norpregna-4,9-diene-3,20-dione 4.9 g of the compound described in Example 32a) is reacted according to the methods described in Examples 4b) and 1e). After chromatography on silica gel with a mixture of ethyl acetate and hexane and digesting the product with diisopropyl ether, 1.52 g of 32b) is obtained.

Flash point: 141° C. (decomposition) $[\alpha]_D^{20}$=−358.8° (CHCl$_3$; c=0.515).

$^1$H-NMR (CDCl$_3$): d=1.19 ppm (s,3H,H-18); 2.22 (s,3H, H-21); 4.84 (s broad,1H,16-methylene); 4.90 (s broad,1H, 16-methylene); 5.68 (s broad,1H,H-4).

Example 33

16-Methylene-14,17-ethano-19-norpregna-4,6-diene-3,20-dione 600 mg of 20,20-[1,2-ethanediylbis(oxy)]-16-methylene-14,17-ethano-19-norpregn-4-en-3-one of Example 32a) is reacted according to the methods described in Examples 2a), 2b) and 1e). After chromatography on silica gel with a mixture of ethyl acetate and hexane and crystallization of the product from diisopropyl ether, 70 mg of 33) is obtained.

$^1$H-NMR (CDCl$_3$): d=1.10 ppm (s,3H,H-18); 2.21 (s,3H, H-21); 4.86 (s broad,1H,16-methylene); 4.92 (s broad,1H, 16-methylene); 5.78 (s broad,1H,H-4); 6.10–6.26 (m,2H, H-6 and H-7).

Example 34

16α-Methyl-14,17-ethano-19-norpregna-4,6-diene-3, 20-dione a) 20,20-[1,2-Ethanediylbis(oxy)]-3-methoxy-16α-[[(methylsulfonyl)oxy]methyl]-14,17-ethano-19-norpregna-1,3,5(10)-triene 11.7 g of the compound described under 28b), dissolved in a mixture of 15 ml of pyridine and 110 ml of dichloromethane, is mixed at 0° C. slowly with 4.7 ml of methanesulfonic acid chloride. After 24 hours at room temperature, it is mixed with concentrated, ice-cold sodium bicarbonate solution. The organic phase is washed three times with concentrated, ice-cold sodium bicarbonate solution, dried on sodium sulfate and filtered. Under reduced pressure, all volatile components are removed. 14.3 g of 34a) is obtained, which is further reacted without purification.

$^1$H-NMR (CDCl$_3$): d=1.11 ppm (s,3H,H-18); 1.31 (s,3H, H-21); 3.02 (s,3H,SO$_2$CH$_3$); 3.68 (s,3H,3-OCH$_3$); 3.82–4.06 (m,5H,20-OCH$_2$CH$_2$O—); 4.12 (dd,J=9 and 10 Hz,1H,16-CH$_2$); 4.80 (dd,J=4 and 10 Hz,1H,16-CH$_2$); 6.62 (d,J=3 Hz,1H,H-4); 6.70 (dd,J=9 and 3 Hz,1H,H-2); 7.20 (d,J=9 Hz,1H,H-1).

b) 20,20-[1,2-Ethanediylbis(oxy)]-3-methoxy-16α-methyl-14,17-ethano-19-norpregna-1,3,5(10)-triene 14.3 g of the compound described under 34a) is suspended in 20 ml of tetrahydrofuran and mixed with 150 ml of a 1 molar solution of lithium triethyl borohydride in tetrahydrofuran. After 5.5 hours of heating under argon, it is left for 15 hours at room temperature and dispersed between ethyl acetate and concentrated ammonium chloride solution. The organic phase is washed with concentrated sodium bicarbonate solution, dried on sodium sulfate, filtered and concentrated by evaporation. After chromatography on silica gel with a mixture of ethyl acetate and hexane, 6.0 g of 34b) is obtained.

Flash point: 132–134° C.

$^1$H-NMR (CDCl$_3$): d=1.01 ppm (s,3H,H-18); 1.19 (d, J=7.5 Hz,16-CH$_3$); 1.30 (s,3H,H-21); 3.78 (s,3H,3-OCH$_3$); 3.83–4.04 (m,5H,20-OCH$_2$CH$_2$O—); 6.62 (d,J=3 Hz,1H,H-4); 6.71 (dd,J=9 and 3 Hz,1H,H-2); 7.22 (d,J=9 Hz,1H,H-1).

c) 3-Methoxy-16α-methyl-14,17-ethano-19-norpregna-1,3,5(10)-trien-20-one 5.96 g of the compound described under 34b) is reacted according to the method described in Example 1e). 5.58 g of 34c) is obtained as crude product.

Flash point: 115–116° C. $[\alpha]_D^{20}$=+51.3° (CHCl$_3$; c=0.530).

$^1$H-NMR (CDCl$_3$): d=0.93 ppm (s,3H,H-18); 0.99 (d, J=7.5 Hz,16-CH$_3$); 2.11 (s,3H,H-21); 3.78 (s,3H,3-OCH$_3$); 6.62 (d,J=3 Hz,1H,H-4); 6.71 (dd,J=9 and 3 Hz,1H,H-2); 7.21 (d, J=9 Hz,1H,H-1).

d) 3-Methoxy-16α-methyl-14,17-ethano-19-norpregna-1,3, 5(10)-trien-20ξ-ol 5.53 g of the compound described under 34c) is dissolved in a mixture of 90 ml of methanol and 130 ml of dichloromethane and mixed in portions with 2.37 g of sodium borohydride. After 2 hours at room temperature, it is mixed with water, acidified with 2N hydrochloric acid and the water phase is extracted twice with dichloromethane. After washing the organic phase with water, concentrated sodium bicarbonate solution and concentrated common salt solution, it is dried on sodium sulfate, filtered and concentrated by evaporation. After chromatography on silica gel with a mixture of ethyl acetate and hexane, 4.28 g of 34d) is obtained.

$^1$H-NMR (CDCl$_3$); d=0.98 ppm (s,3H,H-18); 1.04 (1.13) (d,J=7.5 Hz,16-CH$_3$); 1.24 (1.22) (d,J=6.5 Hz,3H,H-21); 3.78 (s,3H,3-OCH$_3$); 3.88–3.98 (m,1H,H-20); 6.62 (d,J=3 Hz,1H, H-4); 6.71 (dd,J=9 and 3 Hz,1H,H-2); 7.21 (d,J=9 Hz,1H,H-1).

(Signals from the 2nd diastereomer in parentheses)

e) 3-Methoxy-16α-methyl-14,17-ethano-19-norpregna-2,5 (10)-dien-20ξ-ol 4.26 g of the compound described under 34d) is reacted according to the method described in Example 1d). 4.45 g of 34e) is obtained as crude product.

$^1$H-NMR (CDCl$_3$): d=0.94 ppm (s,3H,H-18); 1.02 (d, J=7.5 Hz,16-CH$_3$); 1.20 (d,J=6.5 Hz,3H,H-21); 3.53 (s,3H, 3-OCH$_3$); 3.84–3.96 (m,1H,H-20); 4.64 (s broad,1H,H-2).

(NMR data only for the main diastereomer)

f) 16α-Methyl-14,17-ethano-19-norpregna-4,6-diene-3,20-dione 2 g of the compound described under 34e) is reacted according to the methods described in Examples 1e), 2a), 2b) and 7c). 446 mg of 34f) is obtained.

Flash point: 165° C. $[\alpha]_D^{20}$=+16.4° (CHCl$_3$; c=0.525).

$^1$H-NMR (CDCl$_3$): d=0.98 ppm (s,3H,H-18); 1.00 (d, J=7.5 Hz,3H,16-CH$_3$); 2.11 (s,3H,H-21); 5.78 (s broad,1H, H-4); 6.08–6.22 (m,2H,H-6 and H-7).

Example 35

16α-Methyl-14,17-ethano-19-norpregna-4,9-diene-3, 20-dione 2.5 g of the compound described under 34e) is reacted according to the methods described in Examples 4a), 4b) and 7c). 410 mg of 35) is obtained.

Flash point: 125–126° C. $[\alpha]_D^{20}=-300.7°$ (CHCl$_3$; c=0.530).

$^1$H-NMR (CDCl$_3$): d=0.98 (d,J=7.5 Hz,3H,16-CH$_3$); 1.07 ppm (s,3H,H-18); 2.11 (s,3H,H-21); 5.68 (s broad,1H,H-4).

Example 36

16α,21-Dimethyl-14,17-ethano-19-norpregna-4,9-diene-3,20-dione 3.2 g of the compound described under 34e) is reacted according to the methods described in Examples 4a), 4b), 9a), 7c), 7a) and 1e). 308 mg of 36) is obtained.

$[\alpha]_D^{20}=-274.3°$ (CHCl$_3$; c=0.535).

$^1$H-NMR (CDCl$_3$): d=0.99 (d,J=7.5 Hz,3H,16-CH$_3$); 1.04 (t,J=7 Hz,3H,H-22); 1.08 ppm (s,3H,H-18); 5.69 (s broad, 1H, H4).

Example 37

21-Hydroxy-16α-methyl-14,17-ethano-19-norpregn-4-ene-3,20-dione 1.25 g of the compound described under 34e) is reacted according to the methods described in Examples 1e), 9a), 7c), 5c), 5d), 1e) and 5g). 73 mg of 37) is obtained.

$[\alpha]_D^{20}=+56.4°$ (CHCl$_3$; c=0.250).

$^1$H-NMR (CDCl$_3$): d=0.97 (d,J=7.5 Hz,3H,16-CH$_3$); 0.98 ppm (s,3H,H-18); 4.22 (s broad,2H,H-21); 5.82 (s broad,1H, H-4).

Example 38 a) 17$^2$-Methyl-14,17-etheno-19-norpregn-4-ene-3,20-dione a) 17α-Ethinyl-3-methoxy-15-methylestra-1,3,5(10),15-tetraen-17β-ol At 0° C., acetylene is introduced into 500 ml of tetrahydrofuran for 30 minutes. Then, 230 ml of a 1.6 molar solution of n-butyllithium in hexane is instilled. After another 30 minutes, a solution of 12.1 g of 3-methoxy-15-methyl-estra-1,3,5(10),15-tetraen-17-one (see DE 4326240 A1) in 250 ml of tetrahydrofuran is instilled. After 30 minutes, it is dispersed between semisaturated common salt solution and ethyl acetate, the organic phase with semisaturated and saturated common salt solution is washed, dried on sodium sulfate, filtered and concentrated by evaporation. In this case, crystallization occurs. Overall, 12.12 g of 38a) is obtained.

$[\alpha]_D^{20}=-191.4°$ (CHCl$_3$; c=0.500).

$^1$H-NMR (CDCl$_3$): d=0.95 ppm (s,3H,H-18); 1.90 (s broad,3H,15-CH$_3$); 2.66 (s,1H,17-ethinyl); 3.79 (s,3H, 3-OCH$_3$); 5.40 (s broad,1H,H-16); 6.64 (d,J=3 Hz,1H,H-4); 6.73 (dd,J=9 and 3 Hz,1H,H-2); 7.22 (d,J=9 Hz,1H,H-1).

b) 3-Methoxy-17$^2$-methyl-14,17-etheno-19-norpregna-1,3,5(10)-trien-20-one 12.10 g of the compound described under 38a) is reacted according to the methods described in Examples 1a) and 1b). 8.95 g of 38b) is obtained.

Flash point: 123.5–125° C. $[\alpha]_D^{20}=-207.5°$ (CHCl$_3$; c=0.520).

$^1$H-NMR (CDCl$_3$): d=0.86 ppm (s,3H,H-18); 1.88 (s broad, 3H, 17$^2$-CH$_3$); 2.21 (s,3H,H-21); 3.79 (s,3H,3-OCH$_3$); 5.66 (s broad,1H,H-17$^1$); 6.63 (d,J=3 Hz,1H,H-4); 6.73 (dd, J=9 and 3 Hz,1H,H-2); 7.22 (d,J=9 Hz,1H,H-1).

c) 20,20-[1,2-Ethanediylbis(oxy)]-3-methoxy-17$^2$-methyl-14,17-etheno-19-norpregna-2,5(10)-diene 1.50 g of the compound described under 38b) is reacted according to the methods described in Examples 1c) and 1d). 1.65 g of crude 38c) is obtained.

$^1$H-NMR (CDCl$_3$): d=0.92 ppm (s,3H,H-18); 1.32 (s,3H, H-21); 1.80 (s broad,3H,17$^2$-CH$_3$); 3.56 (s,3H,3-OCH$_3$); 3.83–4.02 (m,4H,20-OCH$_2$CH$_2$O—); 4.65 (s broad,1H,H-2); 5.53 (s broad,1H,H-17$^1$).

d) 17$^2$-Methyl-14,17-etheno-19-norpregn-4-ene-3,20-dione 270 mg of the compound described under 38c) is reacted according to the method described in Example 1e). After HPLC, 126 mg of 38d) is obtained.

$^1$H-NMR (CDCl$_3$): d=0.90 ppm (s,3H,H-18); 1.82 (s broad,3H,17$^2$-CH$_3$); 2.18 (s,3H,H-21); 5.63 (s broad,1H, H-17$^1$); 5.85 (s broad,1H,H-4).

Example 39

17$^2$-Methyl-14,17-etheno-19-norpregna-4,9-diene-3,20-dione 1.41 g of the compound described under 38c) is reacted according to the methods described in Examples 4a) and 4b). After HPLC, 178 mg of 39) is obtained.

$[\alpha]_D^{20}=-306.2°$ (CHCl$_3$; c=0.510).

$^1$H-NMR (CDCl$_3$): d=0.98 ppm (s,3H,H-18); 1.73 (s broad,3H,17$^2$-CH$_3$); 2.18 (s,3H,H-21); 5.67 and 5.73 (s broad,1H,H-4 and H-17$^1$ each).

Example 40

(17$^2$R)-17$^2$-Methyl-14,17-ethano-19-norpregn-4-ene-3,20-dione a) (17$^2$R)-3-Methoxy-17$^2$-methyl-14,17-ethano-19-norpregna-1,3,5(10)-trien-20-one 7.95 g of the compound described under 38b) is reacted according to the method described in Example 12a). 6.97 g of 40a) is obtained.

Flash point: 107.5–109.5° C.

$^1$H-NMR (CDCl$_3$): d=0.94 ppm (s,3H,H-18); 1.07 (d, J=7.5 Hz,3H,17$^2$-CH$_3$); 2.11 (s,3H,H-21); 3.78 (s,3H,3-OCH$_3$); 6.61 (d,J=3 Hz,1H,H-4); 6.72 (dd,J=9 and 3 Hz,1H, H-2); 7.23 (d,J=9 Hz,1H,H-1).

b) (17$^2$R)-20,20-[1,2-Ethanediylbis(oxy)]-3-methoxy-17$^2$-methyl-14,17-ethano-19-norpregna-2,5(10)-diene 3.5 g of the compound described under 40a) is reacted according to the methods described in Examples 1c) and 1d). 4.0 g of crude 40b) is obtained, which is further reacted without purification.

$^1$H-NMR (CDCl$_3$): d=0.99 ppm (s,3H,H-18); 0.99 (d, J=7.5 Hz,3H,17$^2$-CH$_3$); 2.11 (s,3H,H-21); 3.55 (s,3H,3-OCH$_3$); 3.83–4.00 (m,4H,20-OCH$_2$CH$_2$O—); 4.64 (s broad, 1H,H-2).

c) (17$^2$R)-17$^2$-Methyl-14,17-ethano-19-norpregna-4-ene-3,20-dione 0.27 g of the compound described under 40b) is reacted according to the method described in Example 1e). 0.14 g of 40c) is obtained.

$^1$H-NMR (CDCl$_3$): d=0.95 ppm (s,3H,H-18); 1.05 (d, J=7.5 Hz,3H,17$^2$-CH$_3$); 2.05 (s,3H,H-21); 5.79 (s broad,1H, H-4).

Example 41

(17$^2$R)-17$^2$-Methyl-14,17-ethano-19-norpregna-4,6-diene-3,20-dione 1.1 g of the compound described under 40b) is reacted according to the methods described in Examples 1c), 2a) and 2b). 0.21 g of 41) is obtained.

$[\alpha]_D^{20}=+117.3°$ (CHCl$_3$; c=0.450).

$^1$H-NMR (CDCl$_3$): d=0.98 ppm (d,J=7.5 Hz,3H,17$^2$-CH$_3$); 0.99 (s,3H,H-18); 2.08 (s,3H,H-21); 5.68 (s broad, 1H,H-4); 6.11–6.27 (m,2H,H-6 and H-7).

Example 42

(17$^2$R)-17$^2$-Methyl-14,17-ethano-19-norpregna-4,9-diene-3,20-dione 1.4 g of the compound described under 40b) is reacted according to the methods described in Examples 4a) and 4b). 0.56 g of 42) is obtained.

Flash point: 118–120° C. $[\alpha]_D^{20}$=–270.5° (CHCl$_3$; c=0.495).

$^1$H-NMR (CDCl$_3$): d=1.06 ppm (s,3H,H-18); 1.09 (d, J=7.5 Hz,3H,17$^2$-CH$_3$); 2.09 (s,3H,H-21); 5.66 (s broad,1H, H-4).

Example 43

(17$^2$R)-17$^2$,21-Dimethyl-14,17-ethano-19-norpregna-4,9-diene-3,20-dione a) (17$^2$R)-17$^2$, 21-Dimethyl-20,20-[1,2-ethanediylbis(oxy)]-14,17-ethano-19-norpregn-5(10)-en-3-one 3.65 g of the compound described under 40a) is reacted according to the methods described in Examples 7a), 1c), 1d) and 8c). 2.33 g of 43a) is obtained and in addition, 0.63 g of (17$^2$R)-17$^2$, 21-dimethyl-20,20-[1,2-ethanediylbis(oxy)]-14,17-ethano-19-norpregn-4-en-3-one.

$^1$H-NMR (CDCl$_3$): d=0.86 ppm (t,J=7.7 Hz,3H,H-22); 0.99 (s,3H,H-18); 1.00 (d,J=7.5 Hz,3H,17$^2$-CH$_3$); 2.67 and 2.78 (d, J=20 Hz, 1H,H-4 each); 3.90–4.08 (m,4H,20-OCH$_2$CH$_2$O—).

b) (17$^2$R)-17$^2$, 21-Dimethyl-14,17-ethano-19-norpregna-4,9-diene-3,20-dione 2.33 g of the compound described under 43a) is reacted according to the methods described in Examples 4b) and 1e). 0.8 g of 43b) is obtained and in addition, 0.48 g of (17$^2$R)-17$^2$,21-dimethyl-14,17-ethano-19-norpregna-5(10),9(11)-diene-3,20-dione.

$[\alpha]_D^{20}$ for compound 43b)=–285.4° (CHCl$_3$; C=0.515).

$^1$H-NMR (CDCl$_3$) for compound 43b): d=1.00 ppm (t, J=7.5 Hz,3H,H-22); 1.05 (s,3H,H-18); 1.08 (d,J=7.5 Hz,3H, 17$^2$-CH$_3$); 5.67 (s broad,1H,H-4).

$^1$H-NMR (CDCl$_3$) for (17$^2$R)-17$^2$, 21-dimethyl-14,17-ethano-19-norpregna-5(10),9(11)-diene-3,20-dione: d=0.86 ppm (s,3H,H-18); 1.00 (t,J=7.5 Hz,3H,H-22); 1.04 (d,J=7.5 Hz,3H, 17$^2$-CH$_3$); 2.88 (s broad,2H,H-4); 5.59–5.68 (m,1H, H-11).

Example 44

(17$^2$R)-17$^2$,21-Dimethyl-14,17-ethano-19-norpregna-4,9,11-triene-3,20-dione 0.45 g of the compound (17$^2$R)-17$^2$,21-dimethyl-14,17-ethano-19-norpregna-5(10),9(11)-diene-3,20-dione, described in Example 43b), is reacted according to the method described in Example 9c). 0.16 g of 44) is obtained.

$[\alpha]_D^{20}$=–48.1° (CHCl$_3$; c=0.455).

$^1$H-NMR (CDCl$_3$): d=1.00 ppm (s,3H,H-18); 1.02 (d, J=7.5 Hz,3H,17$^2$-CH$_3$); 1.03 (t,J=7.5 Hz,3H,H-22); 5.76 (s broad,3H,H-4); 6.44 (d,J=12 Hz;1H,H-11); 6.48 (d,J=12 Hz; 1H,H-12).

Example 45

(17$^2$R)-17$^2$,21-Dimethyl-14,17-ethano-19-norpregna-4,6-diene-3,20-dione 0.62 g of the compound (17$^2$R)-17$^2$,21-dimethyl-20,20-[1,2-ethanediylbis(oxy)]-14,17-ethano-19-norpregn-4-en-3-one, described in Example 43a), is reacted according to the methods described in Examples 2a), 2b) and 1e). 0.13 g of 45) is obtained.

$^1$H-NMR (CDCl$_3$) for compound 43b): d=0.93–1.02 ppm (m,9H,17$^2$-CH$_3$H-18 and H-22); 5.76 (s broad,1H,H-4); 6.12–6.24 (m,2H,H-6 and H-7).

Example 46

14,17-Ethano-19-norpregna-4,15-diene-3,20-dione a) 15β,16β-Dihydro-3-methoxy[1,3]dioxolo[4',5':15,16]-14,17-etheno-19-norpregna-1,3,5(10)-triene-2',20-dione 56 g of the compound described in Example 1a) is mixed with 90.5 ml of vinylene carbonate and 50 mg of hydroquinone and held at a bath temperature of 170° C. under argon for 18 hours. After all volatile components are removed under high vacuum, the residue is chromatographed on silica gel with a mixture of ethyl acetate and hexane. After crystallization from a mixture of diisopropyl ether and acetone, 56.04 g of 46a) is obtained.

Flash point: 217–217.5° C. $[\alpha]_D^{20}$=–219.8° (CHCl$_3$; c=0.495).

$^1$H-NMR (CDCl$_3$): d=0.94 ppm (s,3H,H-18); 2.30 (s,3H, H-21); 3.79 (s,3H,3-OCH$_3$); 4.99 and 5.76 (2d,J=8 Hz,H-15 and H-16); 6.31 and 6.40 (2d,J=6 Hz, 1H,H-17$^1$ and H-17$^2$ each); 6.66 (d,J=3 Hz,1H,H-4); 6.72 (dd,J=9, 3 Hz,1H,H-2); 7.18 (d,J=9 Hz,1H,H-1).

b) 15β,16β-Dihydro-3-methoxy[1,3]dioxolo[4',5':15,16]-14,17-ethano-19-norpregna-1,3,5(10)-triene-2',20-dione 56 g of the compound described in Example 46a) is reacted according to the method described in Example 12a). 56 g of 46b) is obtained.

Flash point: 223–224° C. $[\alpha]_D^{20}$=–111.2° (CHCl$_3$; c=0.515).

$^1$H-NMR (CDCl$_3$): d=0.94 ppm (s,3H,H-18); 2.20 (s,3H, H-21); 3.78 (s,3H,3-OCH$_3$); 4.68 and 5.48 (2dd,J=1.5 and 9 Hz, 1H,H-17$^1$ and H-17$^2$ each); 6.64 (d,J=3 Hz,1H,H-4); 6.73 (dd,J=9, 3 Hz,1H,H-2); 7.19 (d,J=9 Hz,1H,H-1).

c) 15α,16α-Dihydroxy-3-methoxy-14,17-ethano-19-norpregna-1,3,5(10)-trien-20-one 50 g of the compound described in Example 46b) is heated to boiling with 26 g of potassium carbonate in a mixture of 250 ml of methanol, 500 ml of tetrahydrofuran and 150 ml of water for 6 hours. After substantial removal of the solvent, it is poured on 2 liters of ice water, suctioned off and the filter cake is washed with 1 liter of water. 45.80 g of 46c) is obtained.

$^1$H-NMR (CDCl$_3$): d=0.91 ppm (s,3H,H-18); 2.18 (s,3H, H-21); 3.78 (s,3H,3-OCH$_3$); 3.84–3.93 and 4.62–4.71 (2m, 1H,H-17$^1$ and H-17$^2$ each); 6.63 (d,J=3 Hz,1H,H-4); 6.72 (dd,J=9, 3 Hz,1H,H-2); 7.21 (d,J=9 Hz,1H,H-1).

d) 3-Methoxy-14,17-ethano-19-norpregna-1,3,5(10),15-tetraen-20-one 45.7 g of the compound described in Example 46c) is dissolved in 1.5 liters of dichloromethane and mixed at 0° C. with 150 ml of trimethyl orthoformate as well as 6 g of pyridinium paratoluenesulfonate. After 6 hours at room temperature, the batch is filtered on a silica gel column and concentrated by evaporation at room temperature. The evaporation residue is taken up in 1 liter of acetic anhydride and heated to boiling for 5 hours. After concentration by evaporation, the residue is dispersed between concentrated sodium bicarbonate solution and dichloromethane. After the organic phase is washed with concentrated common salt solution, dried on sodium sulfate, filtered and concentrated by evaporation, it is chromatographed on silica gel with a mixture of ethyl acetate and hexane. 6.75 g of 46d) is obtained. All polar fractions of chromatography are combined and concentrated by evaporation. The residue is heated to boiling with 20 g of potassium carbonate in 800 ml of methanol for 3 hours and poured on 2 liters of ice water, suctioned off and the filter cake is washed with 0.5 liter of water. 27.5 g of the compound described in Example 46c) is obtained, from which another 4.50 g of 46d) is obtained according to the method described in Example 46d).

$[\alpha]_D^{20} = +0.5°$ (CHCl$_3$; c=0.505).

$^1$H-NMR (CDCl$_3$): d=0.91 ppm (s,3H,H-18); 2.23 (s,3H, H-21); 3.79 (s,3H,3-OCH$_3$); 6.22 and 6.13 (2d,J=6 Hz, 1H,H-15 and H-16 each); 6.66 (d,J=3 Hz,1H,H-4); 6.73 (dd,J=9, 3 Hz, 1H,H-2); 7.21 (d,J=9 Hz,1H,H-1).

e) 20,20-[1,2-Ethanediylbis(oxy)]-3-methoxy-14,17-ethano-19-norpregna-2,5(10),15-triene 4.5 g of the compound described in Example 46d) is reacted according to the methods described in Examples 1c) and 1d). 5.33 g of crude 46e) is obtained.

$^1$H-NMR (CDCl$_3$): d=0.98 ppm (s,3H,H-18); 1.32 (s,3H, H-21); 3.56 (s,3H,3-OCH$_3$); 3.93–4.07 (m,4H,20-OCH$_2$CH$_2$O—); 4.65 (s broad,1H,H-2); 5.94 and 6.03 (2d, J=6 Hz, 1H,H-15 and H-16 each).

f) 14,17-Ethano-19-norpregna-4,15-diene-3,20-dione 2.0 g of the compound described in Example 46e) is reacted according to the method described in Example 1c). 1.32 g of crude 46f) is obtained.

Flash point: 131–133° C. $[\alpha]_D^{20} = +32.0°$ (CHCl$_3$; c=0.505).

$^1$H-NMR (CDCl$_3$): d=0.93 ppm (s,3H,H-18); 2.20 (s,3H, H-21); 5.85 (s broad,1H,H-4); 6.05 and 6.19 (2d,J=6 Hz, 1H,H-15 and H-16 each).

Example 47

14,17-Ethano-19-norpregna-4,6,15-triene-3,20-dione 1.2 g of the compound described in Example 46f) is reacted according to the methods described in Examples 2a) and 2b). 0.54 g of 47) is obtained.

Flash point: 138–140° C.

$[\alpha]_D^{20} = -28.7°$ (CHCl$_3$; c=0.480).

$^1$H-NMR (CDCl$_3$): d=0.94 ppm (s,3H,H-18); 2.21 (s,3H, H-21); 5.79 (s broad,1H,H-4); 6.14 to 6.34 (m,4H,H-6 and H-7 and H-15 and H-16).

Example 48

14,17-Ethano-19-norpregna-4,9,15-triene-3,20-dione 3.33 g of the compound described in Example 46e) is reacted according to the methods described in Examples 8c) and 4b). 1.08 g of 48) is obtained.

$[\alpha]_D^{20} = -272.4°$ (CHCl$_3$; c=0.475).

$^1$H-NMR (CDCl$_3$) d=1.01 ppm (s,3H,H-18); 2.21 (s,3H, H-21); 5.70 (s broad,1H,H-4); 6.06 and 6.23 (2d,J=6 Hz,2H, H-15 and H-16).

Example 49

21-Hydroxy-14,17-ethano-19-norpregna-4,9,15-triene-3,20-dione a) 3,3-[1,2-Ethanediylbis(oxy)]-14,17-ethano-19-norpregna-5(10),9(11),15-trien-20-one 1.0 g of the compound described in Example 48) is reacted according to the method described in Example 1c). 0.29 g of 49a) is obtained, as well as 0.7 g of the corresponding 3,20-bisketal.

$^1$H-NMR (CDCl$_3$): d=0.82 ppm (s,3H,H-18); 2.22 (s,3H, H-21); 4.00 (s,4H,3-OCH$_2$OCH$_2$O—); 5.51 (s broad,1H,H-11); 6.04 and 6.22 (2d,J=6 Hz,2H,H-15 and H-16).

b) 21-Hydroxy-14,17-ethano-19-norpregna-4,9,15-triene-3,20-dione 0.28 g of the compound described in Example 49a) is reacted according to the methods described in Examples 5c), 5d), 1e) and 5g). 11 mg of 49b) is obtained.

$^1$H-NMR (CDCl$_3$): d=1.00 ppm (s,3H,H-18); 4.33 and 4.42 (2d,J=20 Hz,2H,H-21); 5.70 (s broad,1H,H-4); 6.12 and 6.15 (2d,J=6 Hz,2H,H-15 and H-16).

Example 50

21-Methyl-14,17-ethano-19-norpregna-4,15-diene-3,20-dione a) 20,20-[1,2-Ethanediylbis(oxy)]-21-methyl-14,17-ethano-19-norpregna-4,15-dien-3-one 6.6 g of the compound described in Example 46d) is reacted according to the methods described in Examples 7a), 8a), 1d) and 8c). 0.605 g of 50a) is obtained, as well as 3.70 g of 20,20-[1,2-ethanediylbis(oxy)]-21-methyl-14,17-ethano-19-norpregna-5(10),15-dien-3-one.

$^1$H-NMR (CDCl$_3$) for compound 50a): d=0.93 ppm (t,J=7 Hz,3H,H-22); 0.99 (s,3H,H-18); 3.98–4.15 (m,4H, 20-OCH$_2$CH$_2$O—); 5.83 (s broad,1H,H-4); 5.96 (s,2H,H-15 and H-16).

$^1$H-NMR (CDCl$_3$) for 20,20-[1,2-ethanediylbis(oxy)-21-methyl-14,17-ethano-19-norpregna-5(10),15-dien-3-one: d=0.94 ppm (t,J=7 Hz,3H,H-22); 0.96 (s,3H,H-18); 2.70 and 2.80 (2d,J=20 Hz,2H,H-4); 3.96–4.14 (m,4H,20-OCH$_2$CH$_2$O—); 5.94 and 6.01 (2d,J=6 Hz,2H,H-15 and H-16).

b) 21-Methyl-14,17-ethano-19-norpregna-4,15-diene-3,20-dione 142 mg of the compound described in Example 50a) is reacted according to the method described in Example 1e). 127 g of 50b) is obtained.

Flash point: 140–141° C. $[\alpha]_D^{20} = +25.4°$ (CHCl$_3$; c=0.495).

$^1$H-NMR (CDCl$_3$): d=0.90 ppm (s,3H,H-18); 1.07 (t, J=7 Hz,3H,H-22); 5.85 (s broad,1H,H-4); 6.05 and 6.20 (2d, J=6 Hz,2H,H-15 and H-16).

Example 51

21-Methyl-14,17-ethano-19-norpregna-4,6,15-triene-3,20-dione 460 mg of the compound described in Example 50a) is reacted according to the methods described in Examples 2a), 2b) and 1e). 210 mg of 51) is obtained.

Flash point: 153.5–154.5° C. $[\alpha]_D^{20} = -37.9°$ (CHCl$_3$; c=0.490).

$^1$H-NMR (CDCl$_3$): d=0.93 ppm (s,3H,H-18); 1.08 (t, J=7 Hz,3H,H-22); 5.80 (s broad,1H,H-4); 6.16 to 6.36 (m,4H, H-6 and H-7 and H-15 and H-16).

Example 52

21-Methyl-14,17-ethano-19-norpregna-4,9,15-triene-3,20-dione 3.7 g of 20,20-[1,2-ethanediylbis(oxy)]-21-methyl-14,17-ethano-19-norpregna-5(10),15-dien-3-one of Example 50a) is reacted according to the methods described in Examples 4b) and 1e). 2.1 g of 52) is obtained.

$^1$H-NMR (CDCl$_3$): d=1.00 ppm (s,3H,H-18); 1.08 (t, J=7 Hz,3H,H-22); 5.70 (s broad,1H,H-4); 6.06 and 6.24 (2d, J=6 Hz,2H,H-15 and H-16).

Examples 53 and 54

53: (21R)-21-Hydroxy-21-methyl-14,17-ethano-19-norpregna-4,9,15-triene-3,20-dione 54: (21S)-21-Hydroxy-21-methyl-14,17-ethano-19-norpregna-4,9,15-triene-3,20-dione 1.72 g of the compound described in Example 52) is reacted according to the methods described in Examples 9a), 5c), 5d), 1e) and 5g). 198 mg of 53) and 250 mg of 54) are obtained.

53: $[\alpha]_D^{20}$=-290.0° (CHCl$_3$; c=0.520).

$^1$H-NMR (CDCl$_3$): d=0.95 ppm (s,3H,H-18); 1.38 (d, J=7 Hz,3H,H-22); 4.43 to 4.56 (m,1H,H-21); 5.68 (s broad, 1H,H-4); 6.15 and 6.22 (2d,J=6 Hz,2H,H-15 and H-16).

54: $[\alpha]_D^{20}$=-218.4° (CHCl$_3$; c=0.515).

$^1$H-NMR (CDCl$_3$): d=0.98 ppm (s,3H,H-18); 1.38 (d, J=7 Hz,3H,H-22); 4.41 to 4.52 (m,1H,H-21); 5.71 (s broad, 1H,H-4); 6.10 and 6.18 (2d,J=6 Hz,2H,H-15 and H-16).

Example 55

16-Methyl-14,17-ethano-19-norpregna-4,15-diene-3, 20-dione a) 3-Methoxy-20-oxo-14,17-etheno-19-norpregna-1,3,5 (10),15-tetraene-16-carboxylic acid methyl ester 20 g of the compound described in Example 1a), 20 ml of propiolic acid methyl ester and 50 mg of hydroquinone are held at a bath temperature of 110° C. in a closed tube under argon for 34 hours. After cooling, removal of volatile components and chromatography of the residue on silica gel with a mixture of ethyl acetate and hexane, 12.66 g of 55a) is obtained.

Flash point: 149–149.5° C. $[\alpha]_D^{20}$=-8.3° (CHCl$_3$; c=0.505).

$^1$H-NMR (CDCl$_3$) d=1.30 ppm (s,3H,H-18); 2.28 (s,3H, H-21); 3.73 and 3.78 (2s, 3H,3-OCH$_3$ and CO$_2$CH$_3$ each); 6.65 (d,J=3 Hz,1H,H-4); 6.73 (dd,J=9 and 3 Hz,1H,H-2); 6.76 and 7.02 (2d, J=6 Hz, 1H, H-17$^1$ and H-17$^2$ each); 7.20 (d, J=9 Hz,1H,H-1); 7.58 (s,1H,H-15).

b) 20,20-[1,2-Ethanediylbis(oxy)]-3-methoxy-14,17-etheno-19-norpregna-1,3,5(10),15-tetraene-16-carboxylic acid methyl ester 10.83 g of the compound described in Example 55a) is reacted according to the method described in Example 1c). 11.46 g of 55b) is obtained.

Flash point: 147–147.5° C. $[\alpha]_D^{20}$=-14.7° (CHCl$_3$; c=0.530).

$^1$H-NMR (CDCl$_3$) d=1.28 ppm (s,3H,H-18); 1.55 (s,3H, H-21); 3.73 and 3.78 (2s, 3H,3-OCH$_3$ and CO$_2$CH$_3$ each); 3.95 to 4.11 (m,4H,20—OCH$_2$CH$_2$O—); 6.64 (d,J=3 Hz,1H,H-4); 6.72 (dd,J=9 and 3 Hz,1H,H-2); 6.67 and 6.80 (2d,J=6 Hz, 1H,H-17$^1$ and H-17$^2$ each); 7.21 (d,J=9 Hz,1H, H-1); 7.50 (s,1H,H-15).

c) 20,20-[1,2-Ethanediylbis(oxy)]-3-methoxy-14,17-ethano-19-norpregna-1,3,5(10),15-tetraene-16-carboxylic acid methyl ester 2.50 g of the compound described in Example 55b) is hydrogenated on 100 mg of palladium on carbon (10%) in a mixture of 250 ml of methanol and ethyl acetate each at normal pressure, until 1 equivalent of hydrogen is taken up. After catalyst is filtered out, concentration by evaporation and chromatography on silica gel with a mixture of ethyl acetate and hexane, 1.99 g of 55c) is obtained.

$^1$H-NMR (CDCl$_3$): d=0.97 ppm (s,3H,H-18); 1.54 (s,3H, H-21); 3.73 and 3.78 (2s, 3H,3-OCH$_3$ and CO$_2$CH$_3$ each); 3.90 to 4.06 (m,4H,20 —OCH$_2$CH$_2$O—); 6.64 (d,J=3 Hz,1H,H-4); 6.72 (dd,J=9 and 3 Hz,1H,H-2); 6.92 (s,1H,H-15); 7.21 (d,J=9 Hz, 1H,H-1).

d) 20,20-[1,2-Ethanediylbis(oxy)]-3-methoxy-14,17-ethano-19-norpregna-1,3,5(10),15-tetraene-16-methanol 2.52 g of the compound, described in Example 55c) and dissolved in 40 ml of tetrahydrofuran, is mixed with 157 mg of zinc chloride. At -78° C., 24 ml of a 1.2 molar solution of diisobutylaluminum hydride in toluene is instilled. Then, it is left for 3.5 hours at this temperature, mixed with water, thawed and extracted with ethyl acetate, the organic phase is washed with concentrated common salt solution, dried on sodium sulfate, filtered and concentrated by evaporation. After chromatography on silica gel with a mixture of ethyl acetate and hexane, 1.46 g of 55d) is obtained.

$^1$H-NMR (CDCl$_3$): d=0.98 ppm (s,3H,H-18); 1.39 (s,3H, H-21); 3.24 to 3.32 (m,1H,16-CH$_2$); 3.78 (s,3H,3-OCH$_3$); 3.94 to 4.13 (m,4H,20 —OCH$_2$CH$_2$O—); 4.18 to 4.26 (m,1H,16-CH$_2$); 6.00 (s broad,1H,H-15); 6.64 (d,J=3 Hz,1H,H-4); 6.71 (dd, J=9 and 3 Hz,1H,H-2); 7.20 (d,J=9 Hz,1H,H-1).

e) 16-[(Acetyloxy)methyl]-20,20-[1,2-ethanediylbis(oxy)]-3-methoxy-14,17-ethano-19-norpregna-1,3,5(10),15-tetraene 1.475 g of the compound, described in Example 55d), in 60 ml of pyridine is mixed at 0° C. drop by drop with 1.3 ml of acetyl chloride. After 1.5 hours at room temperature, it is poured on ice-cold concentrated sodium bicarbonate solution and extracted with ethyl acetate. The organic phase is washed in succession with concentrated sodium bicarbonate solution and common salt solution, dried on sodium sulfate, filtered and concentrated by evaporation. 1.85 g of crude 55e) is obtained.

$^1$H-NMR (CDCl$_3$): d=0.97 ppm (s,3H,H-18); 1.33 (s,3H, H-21); 2.09 (s,3H,acetate); 3.77 (s,3H,3-OCH$_3$); 3.92 to 4.12 (m,4H,20 —OCH$_2$CH$_2$O—); 4.74 and 4.82 (2d,J=1.5 and 20 Hz, 1H,16-CH$_2$ each); 5.95 (s broad,1H,H-15); 6.64 (d,J=3 Hz,1H,H-4); 6.72 (dd,J=9 and 3 Hz,1H,H-2); 7.20 (d,J=9 Hz,1H,H-1).

f) 16-Methyl-14,17-ethano-19-norpregna-4,15-diene-3,20-dione 1.73 g of crude 55e) is reacted according to the methods described in Examples 1d) and 1e). 34 mg of 55f) and 92 mg of the compound described in Example 31b) is obtained.

$^1$H-NMR (CDCl$_3$): d=0.96 ppm (s,3H,H-18); 1.77 (s broad,3H,16-CH$_3$); 2.17 (s,3H,H-21); 5.62 (s broad,1H,H-15); 5.84 (s broad,1H,H-4).

Example 56

15β,16α-Dimethyl-14,17-etheno-19-norpregn-4-ene-3,20-dione a) 20,20-[1,2-Ethanediylbis(oxy)]-3-methoxy-15β-methyl-14,17-etheno-19-norpregna-1,3,5(10)-triene-16α-carboxylic acid methyl ester 200 ml of a 1.6 molar solution of methyllithium in diethyl ether is instilled in 30.47 g of copper(I) iodide in 420 ml of diethyl ether at 0° C. After 30 minutes at this temperature, it is diluted with 500 ml of tetrahydrofuran. After cooling to -50° C., 7.0 g of the compound, described in Example 55b), in 200 ml of tetrahydrofuran is instilled. After heating to 0° C., it is left for 4 hours at this temperature. After the addition of concentrated ammonium chloride solution at -20° C., it is dispersed between water and ethyl acetate, the organic phase is washed in succession with ammonia solution, water and concentrated common salt solution, dried on sodium sulfate, filtered, concentrated by evaporation and the residue is chromatographed on silica gel with a mixture of ethyl acetate and hexane. 5.47 g of 56a) is obtained.

$^1$H-NMR (CDCl$_3$): d=1.18 ppm (d,J=7 Hz,3H,15-CH$_3$); 1.20 (s,3H,H-18); 1.30 (s,3H,H-21); 3.14 (d,J=5 Hz,1H,H-16); 3.62 (s,3H,CO$_2$CH$_3$); 3.78 (s,3H,3-OCH$_3$); 3.79 to 4.13 (m,4H, 20 —OCH$_2$CH$_2$O—); 5.98 and 6.30 (2d,J=6 Hz, 1H,H-17$^1$ and H-17$^2$ each); 6.64 (d,J=3 Hz,1H,H-4); 6.72 (dd,J=9 and 3 Hz,1H, H-2); 7.20 (d,J=9 Hz,1H,H-1).

b) 15β,16α-Dimethyl-14,17-etheno-19-norpregn-4-ene-3, 20-dione 2.0 g of the compound described in Example 56a) is reacted according to the methods described in Examples 28c), 34a), 34b), 1d) and 1e). 303 mg of 56b) is obtained.

$[\alpha]_D^{20}$=+99.8° (CHCl$_3$; c=0.510).

$^1$H-NMR (CDCl$_3$): d=0.88 and 1.05 ppm (2d,J=7 Hz, 3H, 15-CH$_3$ and 16-CH$_3$ each); 1.04 (s,3H,H-18); 2.14 (s,3H, H-21); 5.85 (s broad,1H,H-4); 6.01 and 6.20 (2d,J=6 Hz, 1H,H-17$^1$ and H-17$^2$ each).

Example 57

15β,16α-Dimethyl-14,17-ethano-19-norpregn-4-ene-3,20-dione 1.48 g of the compound described in Example 56a) is reacted according to the methods described in Examples 28c), 34a), 34b), 55c), 1d) and 1e). 223 mg of 57) is obtained.

Flash point: 212–214° C. $[\alpha]_D^{20}$=+21.1° (CHCl$_3$; c=0.505).

$^1$H-NMR (CDCl$_3$): d=0.97 and 1.01 ppm (2d,J=7 Hz,3H, 15-CH$_3$ and 16-CH$_3$ each); 1.08 (s,3H,H-18); 2.09 (s,3H, H-21); 5.82 (s broad,1H,H-4).

Example 58

2',5'-15β,16β-Tetrahydrofuror[3',4';15,16]-14,17-etheno-19-norpregna-4-ene-3,20-dione a) 15β,16β-Dihydro-3-methoxy[2H,5H]furo[3',4':15,16]-14,17-etheno-19-norpregna-1,3,5(10)-triene-2',5',20-trione 10.0 g of the compound described in Example 1a) and 10.0 g of maleic anhydride are stirred for 18 hours under argon at 95° C. After excess maleic anhydride is removed under high vacuum, the residue is crystallized from diisopropyl ether. 9.8 g of 58a) is obtained.

Flash point: 186–187° C. (decomposition) $[\alpha]_D^{20}$=+197.0° (CHCl$_3$; c=0.500).

$^1$H-NMR (CDCl$_3$): d=1.00 ppm (s,3H,H-18); 2.35 (s,3H, H-21); 3.57 and 4.47 (2d,J=8 Hz, 1H,H-15 and H-16 each); 3.79 (s,3H,3-OCH$_3$); 6.41 and 6.49 (2d,J=6 Hz, 1H,H-17$^1$ and H-17$^2$ each); 6.66 (d,J=3 Hz,1H,H-4); 6.73 (dd,J=9 and 3 Hz, 1H,H-2); 7.18 (d,J=9 Hz,1H,H-1).

b) 20,20-[1,2-Ethanediylbis(oxy)-14,17-etheno-19-norpregna-1,3,5(10)-triene-15α,16α-dimethanol 5.45 g of the compound described in Example 58a) is reacted according to the methods indicated in Examples 34d), 7c), 1c) and 28c). 4.13 g of crude 58b) is obtained.

$^1$H-NMR (CDCl$_3$): d=1.01 ppm (s,3H,H-18); 1.42 (s,3H, H-21); 3.48 to 3.58 and 3.60 to 3.69 (2m, 1H,CH$_2$OH each); 3.78 (s,3H,3-OCH$_3$); 3.93 to 4.10 (m,6H,CH$_2$OH and 20-OCH$_2$CH$_2$O—); 5.96 and 6.04 (2d,J=6 Hz, 1H,H-17$^1$ and H-17$^2$ each); 6.63 (d,J=3 Hz,1H,H-4); 6.72 (dd,J=9 and 3 Hz,1H, H-2); 7.19 (d,J=9 Hz,1H,H-1).

c) 20,20-[1,2-Ethanediylbis(oxy)]-3-methoxy-2',5',15β,16β-tetrahydrofuro[3',4':15,16]-14,17-etheno-19-norpregna-1,3,5(10)-triene 4.1 g of the compound described in Example 58b) is cooled in a mixture of 70 ml of dichloromethane and 14 ml of pyridine to 0° C. and mixed drop by drop with a total of 3.34 ml of methanesulfonic acid chloride. After 3 hours of stirring at room temperature, it is mixed with concentrated sodium bicarbonate solution. After 20 minutes, it is dispersed between water and ethyl acetate, the organic phase is washed with concentrated sodium bicarbonate solution and common salt solution, dried on sodium sulfate, filtered, concentrated by evaporation and chromatographed on silica gel with a mixture of ethyl acetate and hexane. 0.81 g of 58c) is obtained.

Flash point: 148–150° C. $[\alpha]_D^{20}$=+135.0° (CHCl$_3$; c=0.480).

$^1$H-NMR (CDCl$_3$): d=1.19 ppm (s,3H,H-18); 1.30 (s,3H, H-21); 3.34 to 3.83 (m,4H,15-CH$_2$ and 16-CH$_2$); 3.79 (s,3H, 3-OCH$_3$); 3.85 to 4.08 (m,4H,20-OCH$_2$CH$_2$O—); 6.12 and 6.18 (2d,J=6 Hz, 1H,H-17$^1$ and H-17$^2$ each); 6.63 (d,J=3 Hz,1H,H-4); 6.72 (dd,J=9 and 3 Hz,1H,H-2); 7.21 (d,J=9 Hz,1H,H-1).

d) 2',5',15β,16β-Tetrahydrofuro[3',4':15,16]-14,17-etheno-19-norpregn-4-ene-3,20-dione 0.41 g of the compound described in Example 58c) is reacted according to the methods indicated in Examples 1d) and 1e). 0.23 g of 58d) is obtained.

Flash point: 163.5–165° C. $[\alpha]_D^{20}$=+149.8° (CHCl$_3$; c=0.485).

$^1$H-NMR (CDCl$_3$): d=1.08 ppm (s,3H,H-18); 2.17 (s,3H, H-21); 3.33 to 3.46 and 3.60 to 3.76 (2m, 2H,15-CH$_2$ and 16-CH$_2$ each); 5.88 (s broad,1H,H-4); 6.21 and 6.27 (2d, J=6 Hz, 1H,H-17$^1$ and H-17$^2$ each).

Example 59

2',5',15β,16β-Tetrahydrofuro[3',4':15,16]-14,17-ethano-19-norpregna-4-ene-3,20-dione 0.4 g of the compound described in Example 58c) is reacted according to the methods indicated in Examples 55c), 1d) and 1e). 0.234 g of 59) is obtained.

Flash point: 187–189° C. $[\alpha]_D^{20}$=+72.8° (CHCl$_3$; c=0.520).

Example 60

14,17-Ethano-18a-homo-19-norpregna-4,15-diene-3,20-dione a) 3-Methoxy-14,17-ethano-18a-homo-19-norpregna-1,3,5(10),15-tetraen-20-one 34.0 g of 3-methoxy-15-methyl-18a-homoestra-1,3,5(10), 15-tetraen-17-one (see DE 3710728 A1) is reacted according to the methods described in Examples 38a), 1a), 58a), and 18a) and then with 2N sodium hydroxide solution in tetrahydrofuran. 2.0 g of the dicarboxylic acid that results is dissolved as crude product in 20 ml of pyridine, mixed with 2.2 g of lead tetraacetate and heated to 70° C. for 10 hours. Then, the reaction mixture is introduced into 4N hydrochloric acid. The precipitate is filtered out and chromatographed on silica gel with a mixture of n-hexane and ethyl acetate. 90 mg of 60a) is obtained.

$^1$H-NMR (CDCl$_3$): d=0.62 ppm (t,J=7 Hz,3H,H-18a); 2.25 (s,3H,H-21); 3.78 (s,3H,3-OCH$_3$); 6.10 and 6.26 (2d, J=6 Hz, 1H,H-15 and H-16 each); 6.65 (d,J=3 Hz,1H,H-4); 6.72 (dd, J=9, 3 Hz,1H,H-2); 7.19 (d,J=9 Hz,1H,H-1).

b) 14,17-Ethano-18a-homo-19-norpregna-4,15-diene-3,20-dione 115 mg of the compound described under 60a) is reacted according to the methods described in Examples 1c), 1d) and 1e). 18 mg of 60b) is obtained.

$^1$H-NMR (CDCl$_3$): d=0.63 ppm (t,J=8 Hz,3H,H-18a); 2.23 (s,3H,H-21); 5.86 (s broad,1H,H-4), 6.03 and 6.24 (2d, J=5 Hz,1H,H-15 and H-16 each).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An intermediate product of formula II

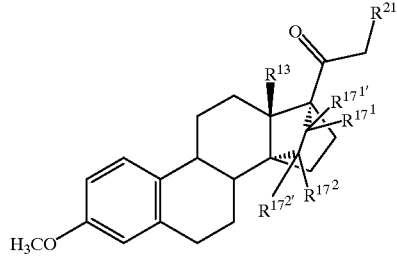

(II)

wherein
- $R^{13}$ is —$C_2H_5$ and $R^{21}$ is H or $C_1$–$C_3$-alkyl, or
- $R^{13}$ is —$CH_3$ and $R^{21}$ is $C_1$–$C_3$-alkyl;
- $R^{17^1}$ and $R^{17^2}$ independently are H or $C_1$–$C_3$-alkyl; and
- $R^{17^{1'}}$ and $R^{17^{2'}}$ are each H, or together form an additional bond.

2. An intermediate product of formula III

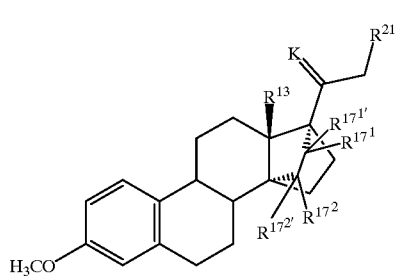

(III)

wherein
- $R^{13}$ is —$CH_3$ or —$C_2H_5$,
- $R^{17^1}$ and $R^{17^2}$ each independently are H or $C_1$–$C_3$-alkyl,
- $R^{17^{1'}}$ and $R^{17^{2'}}$ are each H, or together form a bond,
- K is a ketal protective group, and
- $R^{21}$ is H or $C_1$–$C_3$-alkyl.

3. An intermediate product of formula IV

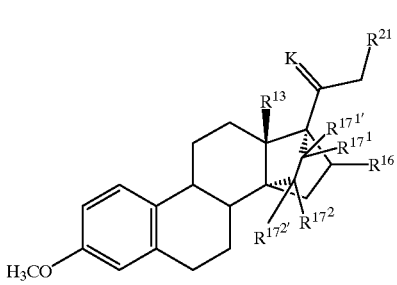

(IV)

wherein
- $R^{13}$ is $CH_3$ or —$C_2H_5$,
- $R^{16}$ is —COOalkyl, wherein alkyl is a $C_1$–$C_4$-alkyl radical; or —$CH_2OH$ or CHO; or methylene,
- $R^{17^1}$ and $R^{17^2}$ each independently is or $C_1$–$C_3$-alkyl,
- $R^{17^{1'}}$ and $R^{17^{2'}}$ each is H or together form a bond,
- K is O or a ketal protective group, and
- $R^{21}$ is H or $C_1$–$C_3$-alkyl.

4. Intermediate products of general formula V

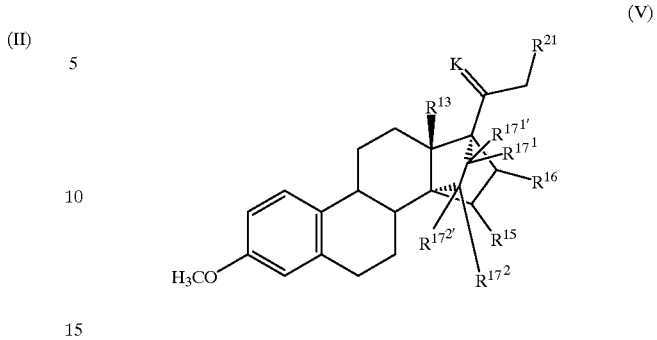

(V)

wherein
- $R^{13}$ is —$CH_3$ or —$C_2H_5$,
- $R^{15}$ and $R^{16}$ together form a ring of partial formula

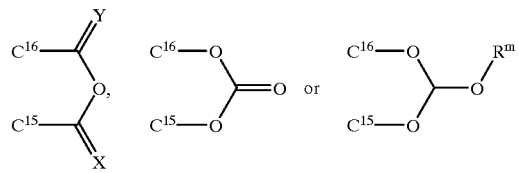

wherein
- X and Y each independently are O or two H atoms, and $R^m$ is $C_1$–$C_3$-alkyl;

or
- $R^{15}$ and $R^{16}$ are each an —OH group; or
- $R^{15}$ and $R^{16}$ together form a bond;

and
- $R^{17^1}$ and $R^{17^2}$ each independently are H or $C_1$–$C_3$-alkyl,
- $R^{17^{1'}}$ and $R^{17^{2'}}$ each are H or together form a bond,
- K is O or a ketal protective group, and
- $R^{21}$ is or $C_1$–$C_3$-alkyl.

5. An intermediate product of formula VI

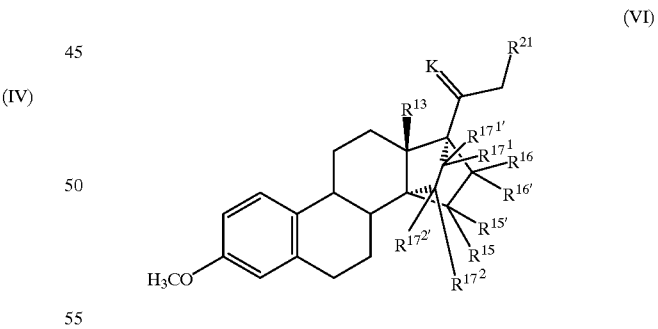

(VI)

wherein
- $R^{13}$ is —$CH_3$ or —$C_2H_5$,
- $R^{15}$ and $R^{16}$ each are H or together form a bond,
- $R^{15'}$ is H or $C_1$–$C_3$-alkyl,
- $R^{16'}$ is —COOalkyl, wherein alkyl is a $C_1$–$C_4$-alkyl radical; or, $CH_2OH$ or CHO; or a $C_1$–$C_3$-alkyl radical,
- $R^{17^1}$ and $R^{17^2}$ each independently are H or $C_1$–$C_3$-alkyl,
- $R^{17^{1'}}$ and $R^{17^{2'}}$ are each H or together form a bond,
- K is O or a ketal protective group, and
- $R^{21}$ is H or $C_1$–$C_3$-alkyl.

6. An intermediate product of formula III of claim 2, wherein K is a 1,2-ethanediylbis(oxy) group or 2,2-dimethyl-1,3-propanediylbis(oxy) group.

7. An intermediate product of formula IV of claim 3, wherein K is a ketal protective group, which is a 1,2-ethanediylbis(oxy) group or 2,2-dimethyl-1,3-propanediylbis(oxy) group.

8. An intermediate product of formula V of claim 4, wherein K is a ketal protective group, which is a 1,2-ethanediylbis(oxy) group or 2,2-dimethyl-1,3-propanediylbis(oxy) group.

9. An intermediate product of formula VI of claim 5, wherein K is a ketal protective group, which is a 1,2-ethanediylbis(oxy) group or 2,2-dimethyl-1,3-propanediylbis(oxy) group.

\* \* \* \* \*